United States Patent [19]

Barsness

[11] Patent Number: 5,107,833
[45] Date of Patent: Apr. 28, 1992

[54] TELEMETRY GAIN ADJUSTMENT ALGORITHM AND SIGNAL STRENGTH INDICATION IN A NOISY ENVIRONMENT

[75] Inventor: Michael S. Barsness, Brooklyn Park, Minn.

[73] Assignee: Medtronic, Inc., Minneapolis, Minn.

[21] Appl. No.: 608,492

[22] Filed: Nov. 2, 1990

[51] Int. Cl.$^5$ .............................................. A61B 5/04
[52] U.S. Cl. ............................ 128/419 PT; 128/903; 128/901
[58] Field of Search ................. 128/901, 903, 419 PT

[56] References Cited

U.S. PATENT DOCUMENTS

| | | | |
|---|---|---|---|
| 4,531,523 | 7/1985 | Anderson | 128/419 PT |
| 4,712,179 | 12/1987 | Heimer | 128/903 |
| 5,024,221 | 6/1991 | Morgan | 128/903 |
| 5,036,869 | 8/1991 | Inahara | 128/903 |

Primary Examiner—William E. Kamm
Assistant Examiner—Scott M. Getzow
Attorney, Agent, or Firm—John A. Rissman; Harold R. Patton

[57] ABSTRACT

A software-controlled, external programmer for transcutaneously programming and receiving data from an implanted medical device providing a real-time indication of the implanted medical device RF telemetry signal strength to the user of the device programmer while automatically optimizing gain level to minimize interference in the presence of noise. The method and apparatus involves monitoring the validity of received intervals or frames uplinked from the implanted medical device to adjust the gain of the RF amplifier in a predetermined range. When noise is detected, indicating a relatively small signal-to-noise ratio, the automatic gain control (AGC) level is decreased, effectively tracking this condition. Similarly, lack of any signal of loss of individual RF pulses causes the AGC level to be increased.

16 Claims, 10 Drawing Sheets

TELEMETRY GAIN ADJUSTMENT ALGORITHM AND SIGNAL STRENGTH INDICATION IN A NOISY ENVIRONMENT

CROSS REFERENCE TO RELATED APPLICATION

Attention is drawn to the commonly assigned, co-pending U.S. patent application Ser. No. 468,407, filed Jan. 22, 1990, in the name of Paul B. Wyborney, et al, which is incorporated herein by reference.

BACKGROUND OF THE INVENTION

1. Field of the Invention

This invention relates to a method and apparatus for controlling the gain of an RF amplifier in response to noise, missing pulses or signal loss and providing a real-time indication of the RF telemetry signal strength to the user of a medical device programmer.

2. Description of the Prior Art

In the field of programmable implanted medical devices, such as cardiac pacemakers, tachyarrhythmia-control devices, implantable drug dispensers and nerve stimulators, it has become common to provide an interactive, transceiver system for both remotely programming operating functions, modes and parameters of the implanted device, and telemetering out data related thereto on command by RF telemetry. In nearly all such active, electronic, implanted medical devices, it has become highly desirable to have the ability to reprogram the device's modes of operation, parameters and other functions and to monitor the performance of the device, both historically and contemporaneously. Such current medical devices are designed to provide two-way telemetry by radio frequency signal transmission between the implanted device and the programming head or wand of the external programmer to provide for the exchange of binary coded transmitted information to enable the aforementioned programming by telemetry-in and the reading out of data stored in the device by telemetry-out.

For example, the Medtronic U.S. Pat. No. 4,253,466 describes an implantable digital, programmable, cardiac pacemaker pulse generator which may be programmed by the programmer described in Medtronic U.S. Pat. No. 4,250,884, both incorporated herein by reference. Such programmers as disclosed in the '884 patent are microprocessor-based and menu-driven under an overall operating routine and subroutines. Such programmers display operating conditions, commands and error messages to prompt the user in the proper use of the programming system. The system of the '466 and 884 patent sets forth the software-controlled programming of a series of Medtronic TM pacemakers, but it does not describe the telemetry-out on command of the external programmer of the programmed commands, electrogram, end of-life indicators and the like that have been developed and implemented in subsequent programming systems.

More recently, microprocessor based programmers have been developed by Medtronic, Inc. and others which are operated under the control of dedicated, plug in ROM modules to enable the operation of the system with regard to specific model or series of models of implanted pulse generators. In such systems, the programmer is incapable of operating until a plug-in module or cartridge has been properly installed. The Medtronic ® MemoryMod TM cartridge enables the physician to apply the programmer to a specific set of pulse generator models. The software cartridge concept allows Medtronic, Inc. to expand and update the application of the programmer to new pulse generators and functional capabilities as they become available.

Referring now to FIG. 1-4, the Medtronic Model 9710, 9710A or 9710E programming system (hereinafter the Model 9710 system) is depicted. In FIG. 1, the programmer 10, printer 12, programming head 14 and ECG cable and electrode leads assembly 16 is depicted in a simplified form. The MemoryMod cartridge is installed in programmer 10 which includes within its case the micro processor based computing system, an LCD display, a keyboard, and an AC or battery power supply. The programmer 10 is connected to a printer 12 in order to provide a printed record of values programmed into the implanted device or received from the implanted device or ECG cable and electrode leads assembly. Compatible Medtronic printers include the Model 9712 printer and the Model 9751 system enhancement module high-speed printer. The programming head 14 must be connected for all programming and telemetry functions to the programmer 10 and will be described in greater detail hereafter. The ECG cable and electrode leads assembly 16 is required for the functions that detect the electrocardiogram and/or pacemaker signals via skin electrodes, including the "automatic threshold," "measure," and programming confirmation by way of the program confirmation indicator emitted by the pacemaker (as an alternative to confirmation by telemetry). The processing of input commands applied by way of the keyboard on the programmer to the programming system, the formatting of data for telemetry via the programming head 14, and the processing of signals picked up from skin electrodes via ECG cable and electrode leads 16 is under the control of the software contained within the MemoryMod cartridge. The programming head 14 may comprise the Medtronic Model 9713 or 9713D programming head.

In FIG. 2, the ECG cable and electrode leads assembly 16 is depicted attached via disposable skin electrodes 18 to a patient's chest. The ECG cable and patient electrodes depicted in FIG. 2 are required for programmer functions requiring detection of cardiac and pacemaker signals as mentioned hereinbefore. However, the system may be used without the assembly 16 to program data into the implanted pacemaker or interrogate the pacemaker to telemetry-out program values and data. In current implanted pacemakers, confirmation of a programming transmission occurs by automatic transfer of data via telemetry-out. Use of the ECG cable and electrode leads assembly 16 is not required for programming confirmation with these devices. However, if telemetry is not received because of strong electrical interference, the programmer will attempt to confirm the transmission by surface detection of the PCI (program confirmation indicator) issued by the pulse generator. This method of program confirmation can occur only if the programmer is connected to electrodes on the patient. As described hereinafter, improvements of the present invention are directed toward the reduction or elimination of failures in telemetry-out because of strong electrical interference.

Furthermore, advanced programming and telemetry systems envisage the transmission of the patient s electrogram directly from the pacing electrodes in contact with the heart to the programmer via the RF telemetry link in order to provide near-field and/or far field electrograms directly from the myocardium. In such systems, the effects of electrical interference and other noise on the telemetry transmission is of concern. Medtronic U.S. Pat. No. 4,556,063 (incorporated herein by reference) describes such a system for telemetering out both digital and analog data.

In order to initiate and complete all programming and telemetry functions, the programming head 14 must be properly positioned over the pulse generator so that the POSITION HEAD indicator lights go out FIG. 3 depicts the positioning of the programming head 14 against the patient's skin overlying the implanted pulse generator. The optimum positioning of thelprogramming head over the implanted pulse generator 20 is depicted in FIG. 4. In use, after the programming system is coupled together as depicted in FIGS. 1 and 2 and the pulsegenerator model is keyed into the keyboard of the programmer 10, the POSITION HEAD indicator LED 22 lights up and remains lit until a telemetry link is established between the telemetry head 14 and the implanted device 20. The indicator LED 22 goes out to indicate when the programming head is properly positioned over the implanted house generator 20. For all programming and telemetry functions, the programming head 14 must be positioned so that the POSITION HEAD indicators go out.

In the system depicted in FIGS. 1 through 4, while the programming head is held in position over the pulse generator 20, the POSITION HEAD indicator is periodically flashed each time the programmer 10 receives an invalid interval and adjusts the telemetry signal sensitivity for best reception. If the telemetry link is lost due to programming head reposition or interference, the indicator LED 22 comes on steadily. While the POSITION HEAD indicator LED 22 is on, the programming head 14 may emit a radio frequency "search" signal used to establish a telemetry link with a pulse generator 20. It is desirable to avoid prolonged application of the RF search signal since the search signal can be sensed by the pulse generator and could occasionally cause unintentional inhibition or triggering of the pulse generator 20.

The pulse generator 20 contains a reed switch responsive to the externally applied magnetic field of the programmer head 14 and an RF signal transceiver circuit for receiving, amplifying and processing telemetered-in programming or interrogation commands. Actuation of the pulse generator reed switch and signal transmission and reception is affected by the programming head position and its distance from the pulse generator 20.

The presence of electrical interference or noise strong enough to interrupt reception of telemetry from the implanted pulse generator can affect operation of the POSITION HEAD indicator lights and telemetry functions, including programming confirmation. In such cases, the POSITION HEAD indicator LED 22 may not go out, or a "TOO MUCH INTERFERENCE" or "NO TELEMETRY" message may appear in the LCD following use of a programming or telemetry function.

Hospital operating rooms, catherization laboratories and even physicians' offices are often noisy electrical environments, and such noise has been found on occasion to interfere with the proper programming or interrogation of an implanted pacemaker. Such programming and interrogation of the implanted pacemaker's function is commonly undertaken as part of the surgical implant of the implanted pulse generator. Other equipment in the operating room or in adjoining rooms or floors of the facility may generate severe electrical noise. To ensure the safety of the patient, prior systems, as explained above, have been designed conservatively to avoid misprogramming once acquisition has been obtained by closure of the reed switch of the implanted pulse generator.

To minimize the effects of strong electrical interference, the Model 9713D programming head is provided with a manually controlled, five position, telemetry receiver gain control. The instructions for use with the Model 9713D programming head indicate that in the initial operation of the programmer, the gain control should be set to its highest gain to provide the most sensitive setting. However, if the POSITION HEAD indicator lights did not go out, and if several repositions of the programming head are unsuccessful, then the user is instructed in the physician's manual to reduce the receiver sensitivity by turning the gain control to a lower setting and again repositioning the programming head for each gain setting until a setting is found that provides proper operation. Similarly, if during the use of the telemetry function or confirmation of a programming transmission, the message "TOO MUCH INTERFERENCE" or "NO TELEMETRY" appears on the programmer display, then again sensitivity is to be reduced until a setting and positioning of the programming head is found that provided proper operation.

In response to the above-described disadvantages of the prior art system, attempts have been made to provide automatic gain control circuitry (see for example, U.S. Pat. No. 4,562,840) and software subroutines e.g., those within the Medtronic MemoryMod cartridges, described hereinafter as the "old algorithm" and specifically disclosed in Medtronic U.S. Pat. No. 4,531, 523, incorporated herein by reference. As mentioned hereinbefore, the POSITION HEAD indicator light LED 22 on the programming head 14 indicates proper positioning of the programming head 14 over the implanted pulse generator 20 by going out. This is accomplished by resident software within the MemoryMod cartridges that monitors the intervals of time between RF pulses received by the programmer.

As described in Medtronic U.S. Pat. No. 4,542,532, incorporated herein by reference, the RF telemetry pulse signal is centered at 175 kHz with a band width of 25 kHz. The RF signals are pulse interval modulated with a "1" or "0" interval value. These intervals are monitored on a continuous basis by one of the processors in the programmer. If any valid interval is detected as within the valid range (732±15% micro seconds for a binary "0" and 1098±15% micro seconds for a binary "1"), a flag is set indicating this state. If any interval is received outside of the valid ranges, the flag is reset. Once every 250 ms., another processor within the programmer examines the contents of this flag. If the flag is set indicating the valid interval collected, the POSITION HEAD LED 22 is turned off. If the flag indicated an invalid collected interval, the LED 22 would be turned on. This POSITION HEAD indicator LED 22 is used by physicians to validate the condition of the link prior to requesting information from the IPG. The information uplinked by telemetry from the implanted pulse generator 20 lasts 300 ms., while the test to determine the validity of the link checks lasts 1 ms. and indicates a good or bad telemetry link, depending on the state of the single collected interval prior to the most recent 250 ms. check.

Moreover, the old algorithm set the automatic gain control at maximum to start telemetry-in and operated in an essentially uni-directional fashion to decrease the maximum gain under certain conditions to be described hereinafter. The old algorithm disadvantageously tended to leave the system operating at high gain and thus susceptible to the detection of noise in a noisy environment.

Even with these improvements incorporated in the prior art systems described above noise interference is still encountered. The physician is still instructed in the physician's manual to either identify the source of interference and eliminate it or move the patient and programmer to another location to avoid its effects.

As mentioned hereinbefore, the prior system provided the user with the POSITION HEAD LED 22 and two visual commands, or prompts, in response to weak or noisy signal reception from the implanted pulse generator 20. It would be desirable to provide the physician with a more effective automatic gain control algorithm and with a more precise indication of signal strength in relation to the then prevailing AGC setting, in order to ascertain the cause of difficulties in programming or telemetry.

SUMMARY OF THE INVENTION

It is thus an object of the present invention to provide an improved automatic gain control algorithm for discriminating telemetry signals from noise.

It is a further object of the present invention to provide telemetry signal strength display to the user of programmer.

The difficulties and deficiencies with the prior software and hardware implementations of automatic gain control and signal strength indication are alleviated and corrected in accordance with the present invention by a telemetry method and apparatus implemented in software algorithms for controlling the automatic gain control and providing a signal strength numeric display in a programming system.

The invention comprises a software controlled, external programmer for transcutaneously programming and receiving data from an implanted medical device providing a real time indication of the implanted medical device RF telemetry signal strength to the user of the device programmer while automatically optimizing gain level to minimize interference in the presence of noise. The method and apparatus involves monitoring the validity of received intervals or frames uplinked from the implanted medical device to adjust the gain of the RF amplifier in a pre-determined range. When noise is detected, indicating a relatively small signal-to-noise ratio, the automatic gain control (AGC) level is decreased, effectively tracking this condition. Similarly, lack of any signal or loss of individual RF pulses causes the AGC level to be increased. The signal strength algorithm utilizes this real-time monitoring of signal integrity and signal-to-noise ratio to provide an indication to the user. In addition to the use of current gain level, a secondary factor is included to provide stability of link factor to the signal strength indication to decrease it in the event that a significant quantity of momentary link instabilities are detected. The telemetry gain adjustment algorithm begins operation at minimum signal level, increasing gain value every 45 ms. until a maximum gain level is reached. When at maximum, the gain is reset to minimum, restarting the search. When valid telemetry signals are received, the gain is stabilized for the duration of uplink telemetry transmission.

BRIEF DESCRIPTION OF THE DRAWINGS

These and other advantages of the present invention will become more apparent by referring to the following detailed description and accompanying drawings in which.

DESCRIPTION OF THE PREFERRED EMBODIMENTS OF THE INVENTION

As stated hereinbefore, the present invention comprises an improvement in the automatic gain control of an amplification stage of the uplink or telemetry-out circuitry of the programmer system of FIG. 1-4, wherein the improvement is implemented in software, as well as the provision of a signal strength indicator for providing the user with a visual alpha-numeric readout of the prevailing signal strength during uplink telemetry. The prevailing signal strength is derived from the automatic gain control factor developed at the point when the minimum gain is set.

Figure 5:
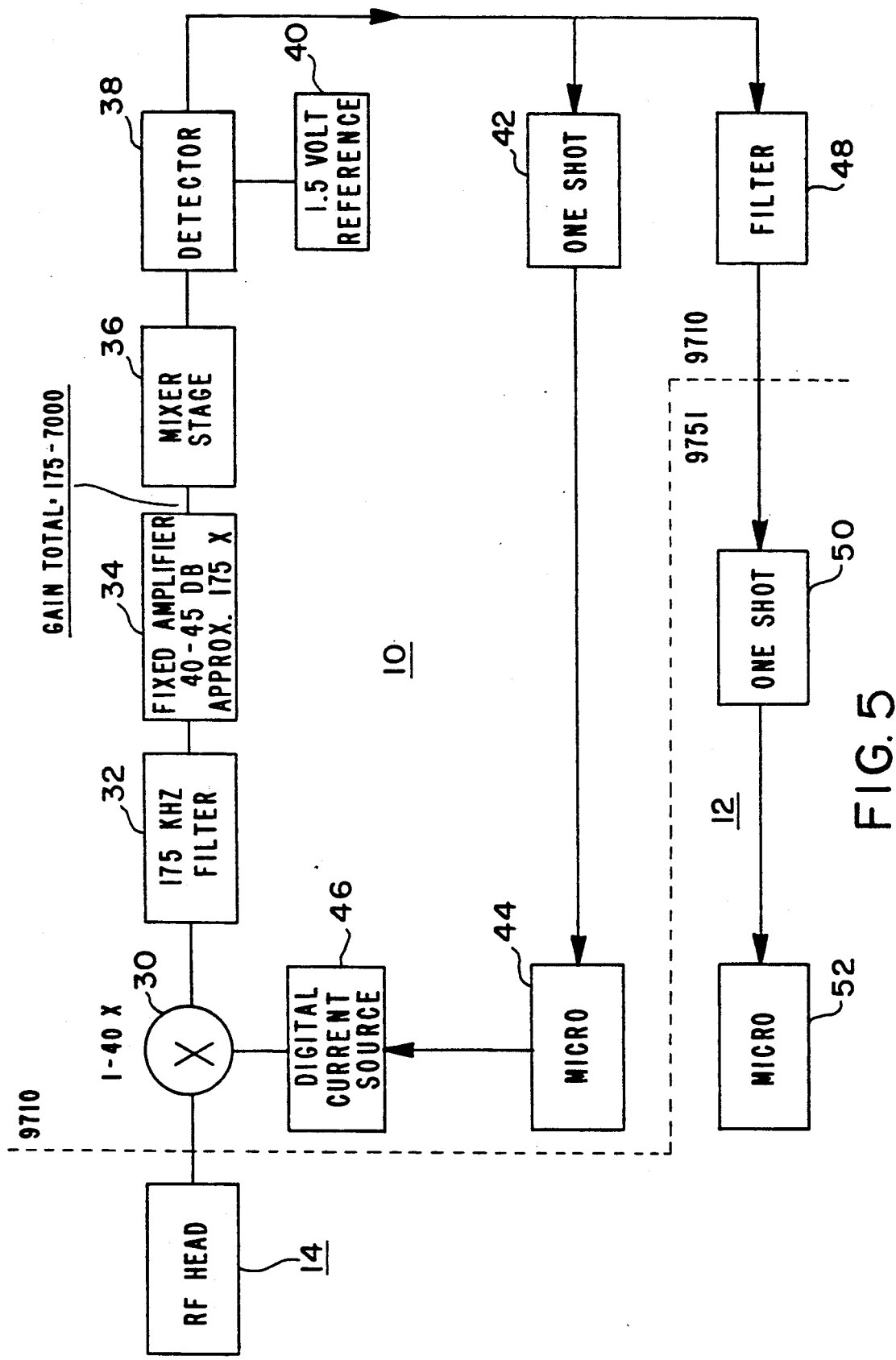
FIG. 5 depicts in block diagram form the receiver stages within the programmer depicted in FIG. 1 for receiving programming confirmation and telemetered-out data.

Referring now to FIG. 5, the Model 9710 receive system block diagram depicted therein provides a simplified representation of the automatic gain control and associated circuitry. The block diagram of FIG. 5 shows the interrelationship of the variable gain amplification stage and microprocessor in the programmer 10 with the radio frequency programming head 14 and printer 12.

The programmer 10 includes the 1 to 40 adjustable gain amplification stage 30 which receives its input signals from RF head 14 during uplink telemetry, amplifies those signals in accordance with the gain factor and applies those signals through 175 kHz band pass filter 32 to fixed amplifier 34. The total gain of the system at the output of fixed amplifier 34 varies between 175 and 7,000. The amplified gain signals are applied to a mixer stage 36 and detector 38 which compares the amplified signal to a 1.6 volt reference 40 and provides an output signal when the amplified and filtered signal exceeds the reference.

Figure 10:
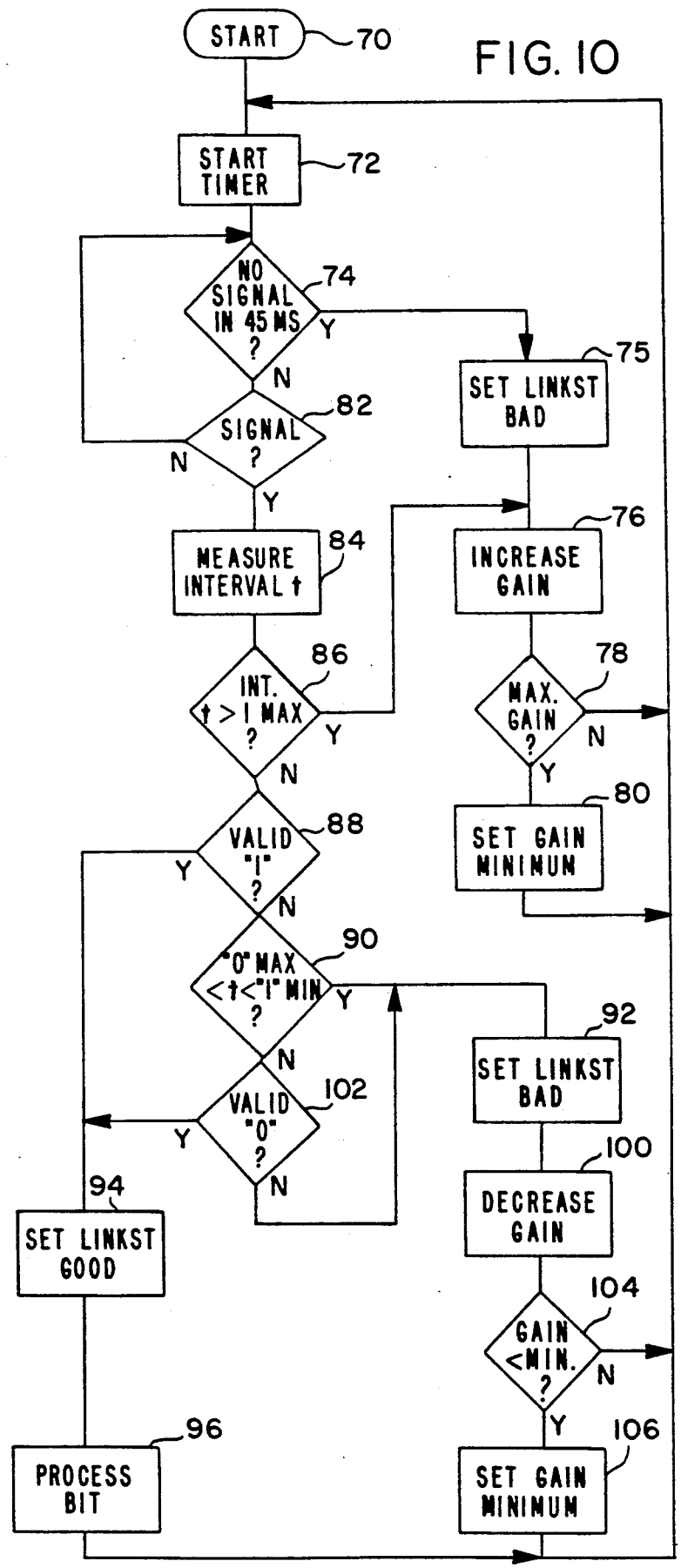
FIG. 10 is a flow chart of the new algorithm for automatically adjusting the gain control.
Figure 11:
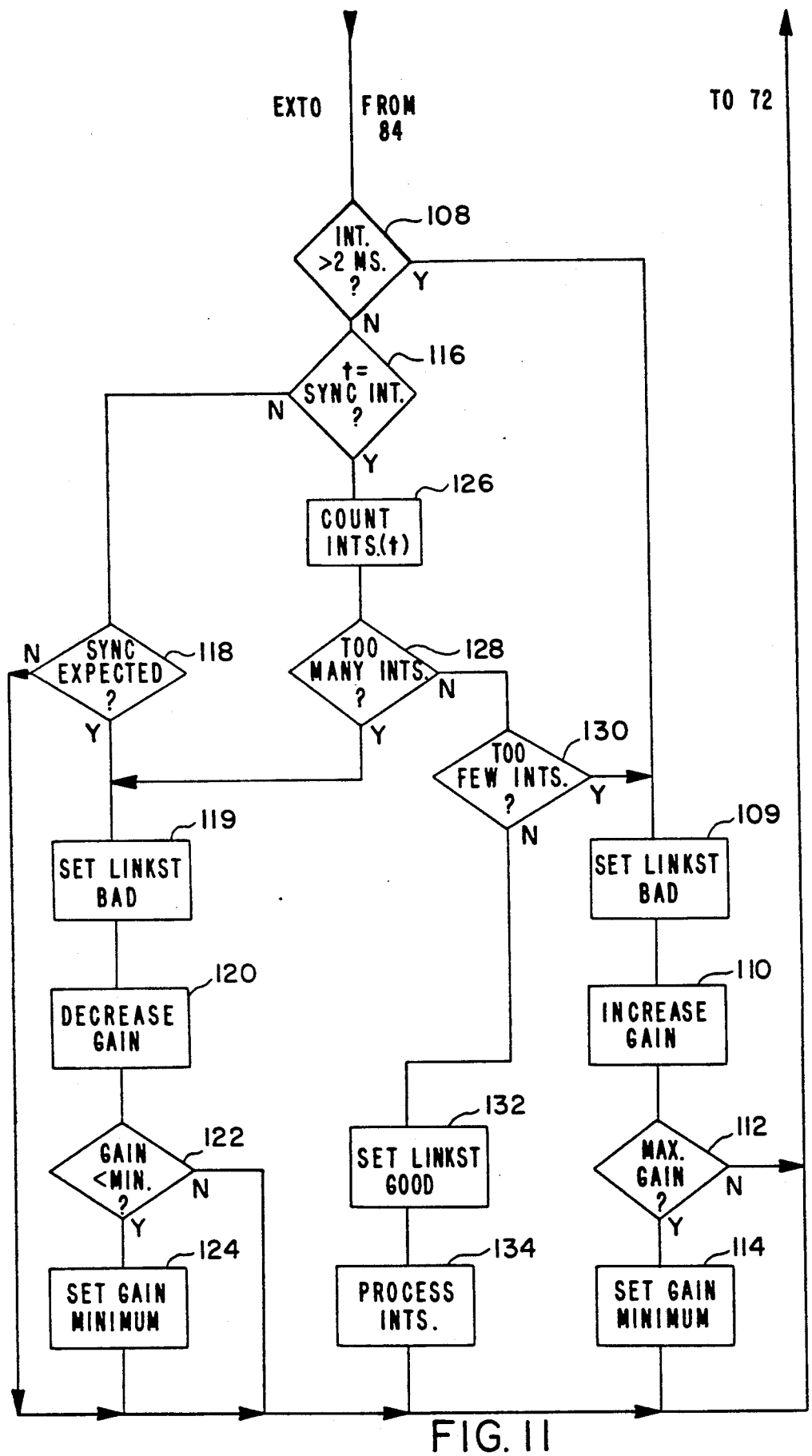
FIG. 11 is a modified flow chart of the new algorithm of FIG. 10 usable with data frame telemetry format.

The output signal is applied to one-shot 42 to develop an interrupt signal applied to a flag input of a peripheral processing unit (PPU) microprocessor 44 which is used in the Model 9710 to process the RF burst transmitted by the IPG. This processor 44 is interrupted each time an RF burst is detected. Under normal situations (no programming of the IPG taking place), the PPU microprocessor 44 is in an "idle" mode. In this mode, interrupts are enabled, and the function of the PPU under software control of FIGS. 10 or 11 is to adjust the automatic gain value provided by the digital current source 46 to maintain a sufficient signal level for future communications. This automatic gain value controls the gain of the RF amplifier in 2 dB steps. processing unit (MPU), the PPU under software control of FIG. 12 develops and provides the signal strength indication that is displayed on the programmer LCD to assist the user in positioning the programming head over the pulse generator. Once valid uplink telemetry intervals are detected, the gain and signal strength values are frozen and the system shifts operation from the idle or acquisition mode to the uplink telemetry mode for receiving and processing bit or frame format data.

The RF burst pulse (centered at 175 kHz) is detected by detector 38 and is also filtered in filter 48 and transmitted to the printer 12. The one shot 50 develops a further signal applied to a resident microprocessor 52 for processing in order to provide a print out if commanded to do so by instructions entered in the keyboard of programmer 10.

Figure 6:
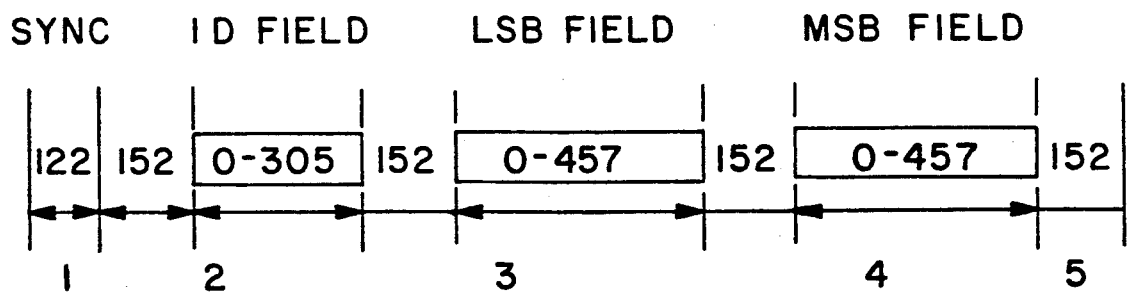
FIG. 6 depicts data bit and frame telemetry formats of dow and uplink-telemetered data.
Figure 6:
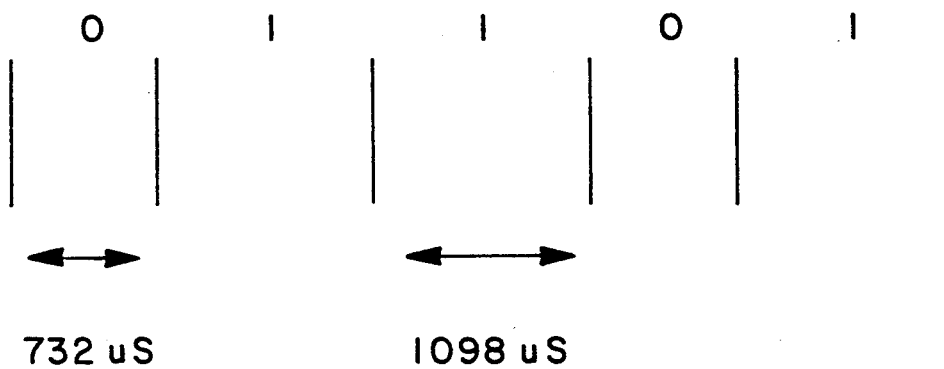
Figure 6:
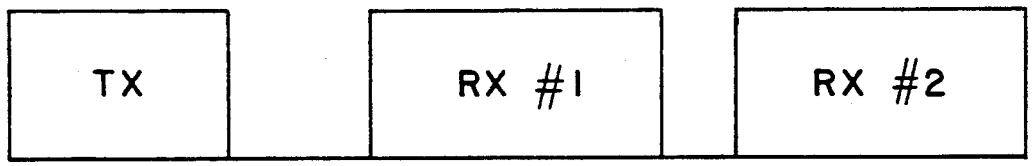

Turning now to FIG. 6, a bit based and frame based telemetry format for uplink and downlink telemetry is generally depicted in the two top most sections of the drawing. The down and uplink data transmission format for both the bit-based and frame-based telemetry formats is shown in the lower portion of FIG. 6. The bit-based telemetry format is to be distinguished from the frame-based telemetry format to be described hereinafter. The new automatic gain control and signal strength indication algorithms of the present invention may be implemented with either telemetry format in a fashion described hereinafter.

Basically, the down and uplink telemetry transmission format involves the transmission of hundreds of frame or data bits in each block labeled "TX," "RX No. 1" and "RX No. 2." During the TX block, the external programmer transmits by downlink telemetry an interrogate command or a programming command which is followed by the uplink telemetry of the data stream from the implanted pulse generator in blocks RX No. 1 and RX No. 2. During uplink telemetry, the implanted pulse generator transmits out the data in block RX No. 1 and then repeats the same transmission in block RX No. 2, so that the external programmer can compare the two data streams for error detection.

The bit-based data transmission of ones and zeros is illustrated immediately above the down and uplink data transmission format illustration of FIG. 6. The data bits "1" and "0" are represented by intervals between 175 kHz RF burst of 1,098 and 732 micro-seconds (plus or minus 15% tolerances), respectively. The automatic gain control algorithm of the present invention compares the 1,098 and 732 micro-second intervals against intervals between received signals to determine whether or not the received signals represent noise or valid data bits in a manner to be described hereafter.

An illustration of one frame of frame-based data transmission appears immediately above the illustration of the intervals between data bits. The frame-based telemetry format consists of individual frames of uplink telemetry RF pulses that convey data by pulse position modulation. Each valid frame is 1.95 ms in length and contains five intervals between the leading RF sync pulses which bound the individual frames.

A valid frame possesses a first sync interval between two RF pulses equal to 122 micro-seconds. The next interval is a "dead" zone of 152± micro seconds. The next interval may vary in length from 0 to 305 micro seconds in 30.5 micro second steps, identifying the type of data (ID) transmitted. The actual detected interval is normalized to the beginning of the ID field and divided by the 30.5 micro-second clock to yield a value from 0 to 10.

Two further 152 micro-second dead zone intervals separate the ID field, the least significant nibble (LSN) field and the most significant nibble (MSN) field. The LSN and MSN field intervals are normalized to the beginning of each respective field and divided by 30.5 to develop a value between zero and fifteen. The last 152 micro-second interval fills out the frame length to 1.95 ms. Within each 1.95 ms. frame there should be 5 intervals separated by 175 kHz signals.

The cross-referenced '407 application describes the frame format telemetry in greater detail. For purposes of this application, the programmer is required to be able to detect and decode both bit based and frame-based data streams since both are presently employed in earlier and more recent generation implanted pulse generators.

Figure 7:
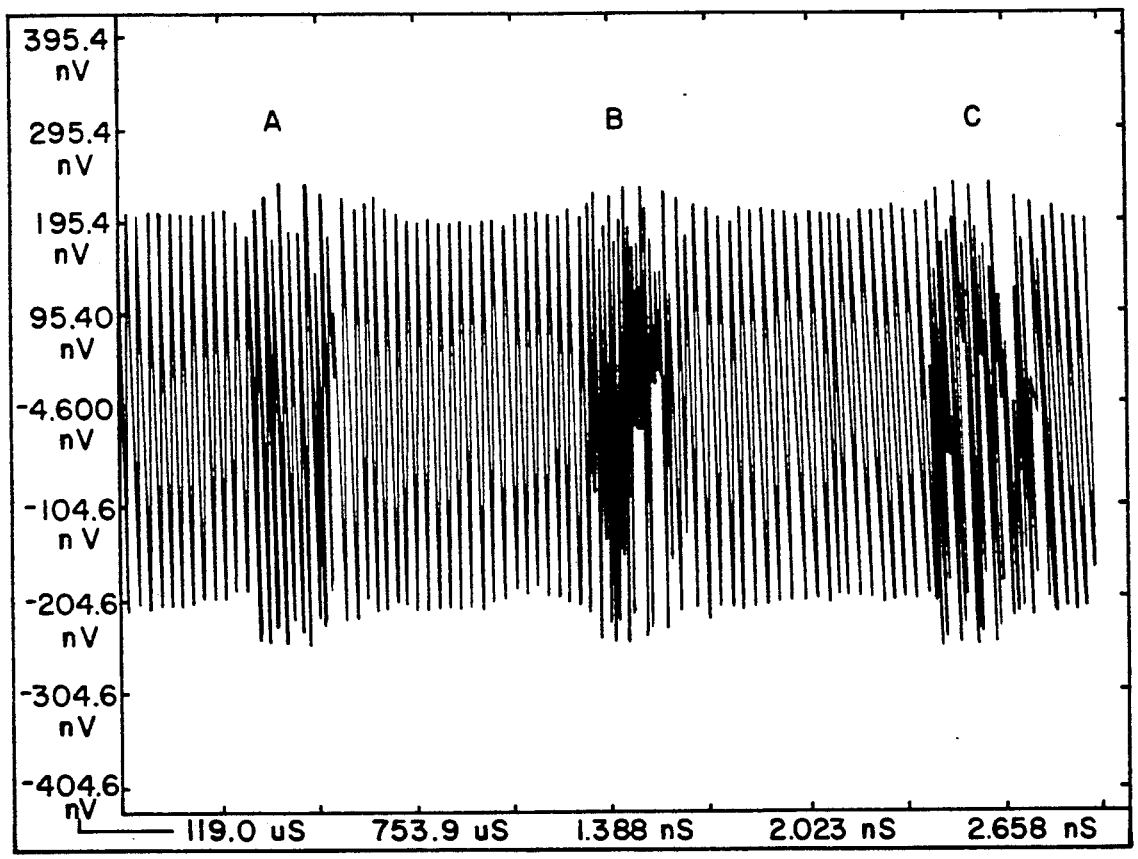
FIG. 7 depicts the RF signal at the high gain setting of the automatic gain control typically achieved by the old algorithm in a relatively normal background noise environment.
Figure 8:
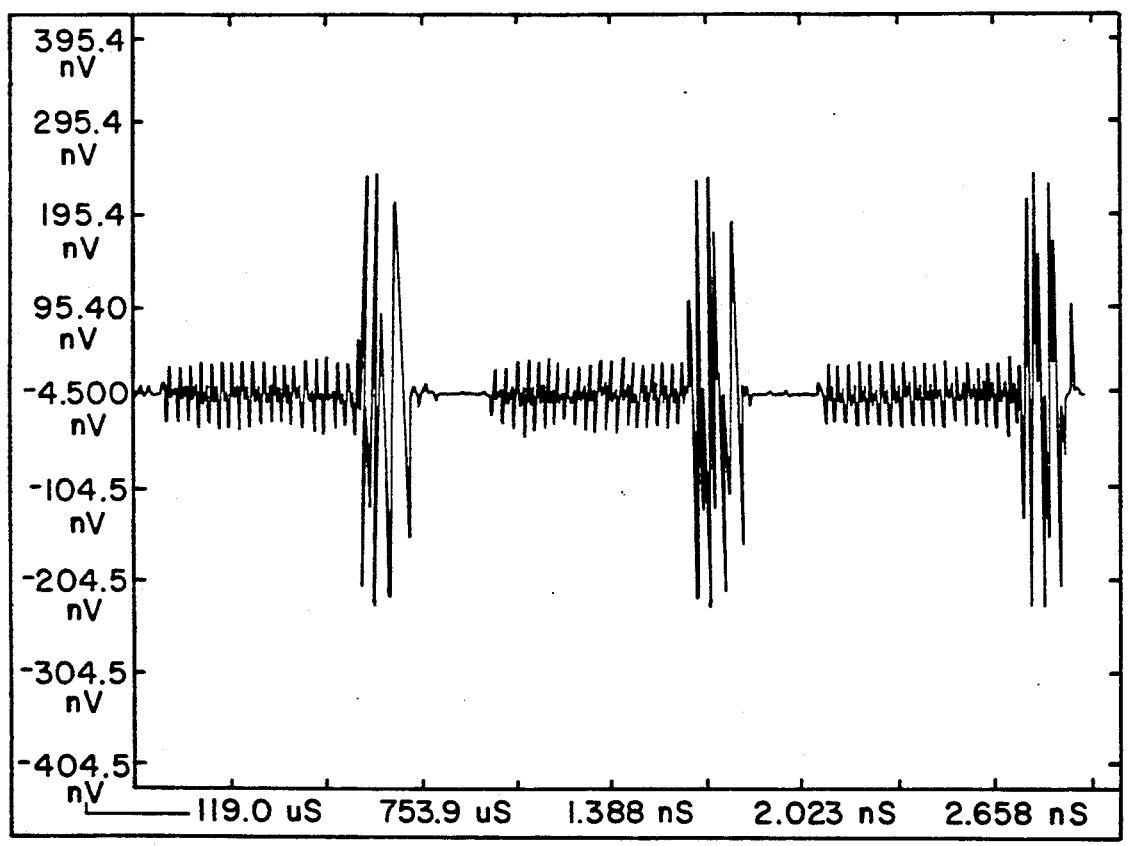
FIG. 8 depicts the RF signal at the low gain setting of the automatic gain control typically achieved by the new algorithm in a relatively normal background noise environment.

FIGS. 7 and 8 depict representations of the RF uplink telemetry signals in the presence of noise at high gain and low gain, respectively. The typical noisy signal at high gain is depicted in FIG. 7 and contains high amplitude, closely-spaced noise excursions of virtually equal amplitude to the 175 kHz RF burst pulses depicted at A,B, and C. Thus, based on amplitude discrimination at high gain, each noise impulse would be confused with a 175 kHz RF telemetry burst, and the pulse interval modulated telemetered signal could not be decoded in the peripheral processing unit and associated software. Conversely, the typical low gain signal depicted in FIG. 8 provides adequate signal amplitude differentiation to discriminate the RF transmitted burst pulses from background noise and to decode either the bit or frame formatted, pulse interval modulated data transmitted from the implanted pacemaker. The ne algorithm of the present invention seeks to maintain the gain at or near the low gain setting rather than at the highest gain possible in the presence of noise.

Figure 4:
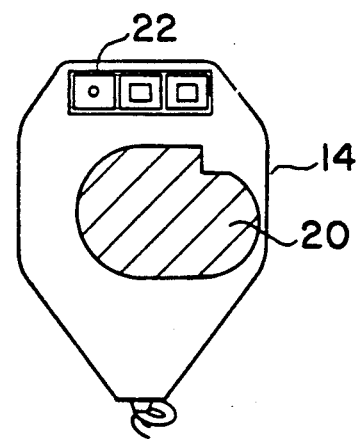
FIG. 4 depicts the optimum programming head position in relation to the implanted pulse generator.

In this regard, it should be noted that implanted pacemaker pulse generators of the type described in the aforementioned U.S. Pat. No. 4,556,063, provide RF telemetry-out signals in the 250 to 300 mv peak-to-peak range, assuming a two inch gap between the implanted pulse generator 20 and the programming head 14 arranged as depicted in FIG. 4. The minimum threshold necessary to ensure reliable detection is approximately 300-320 mv peak-to-peak. The output of the gain amplifier 30 of FIG. 5 clips at a level of about 500 mv peak-to peak. This level is attained with the lowest output implantable pulse generator at a gain value of about 5 in a range of 0 to 9. Any amplification above this value raises the noise level with no increase in RF signal strength, resulting in the typical signal at high gain depicted in FIG. 7. In accordance with the present invention, the new software algorithm limits the gain to a value of about 7. This value allows ample signal strength for even the lowest output implantable pulse generator without allowing the gain to exceed the noise threshold in a "normal" operating environment.

Figure 1:
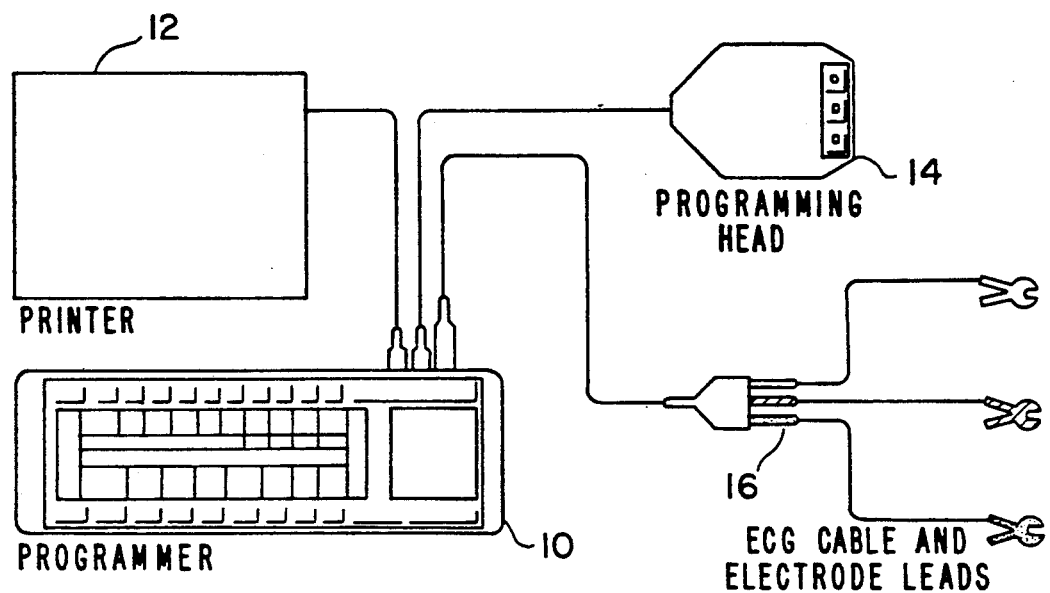
FIG. 1 depicts the programmer system hardware of the prior art in which the software implemented, automatic gain control and sensitivity indicator of the present invention may be implemented.
Figure 2:
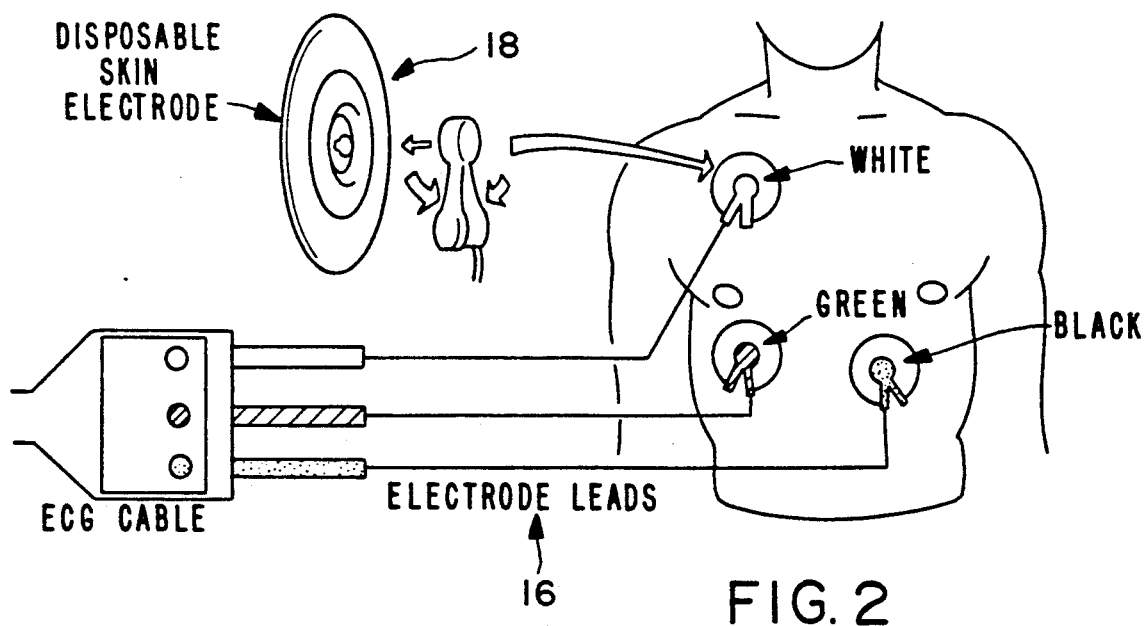
FIG. 2 depicts the connection of the programmer of FIG. 1 to skin electrodes through the ECG cable and electrode leads.
Figure 3:
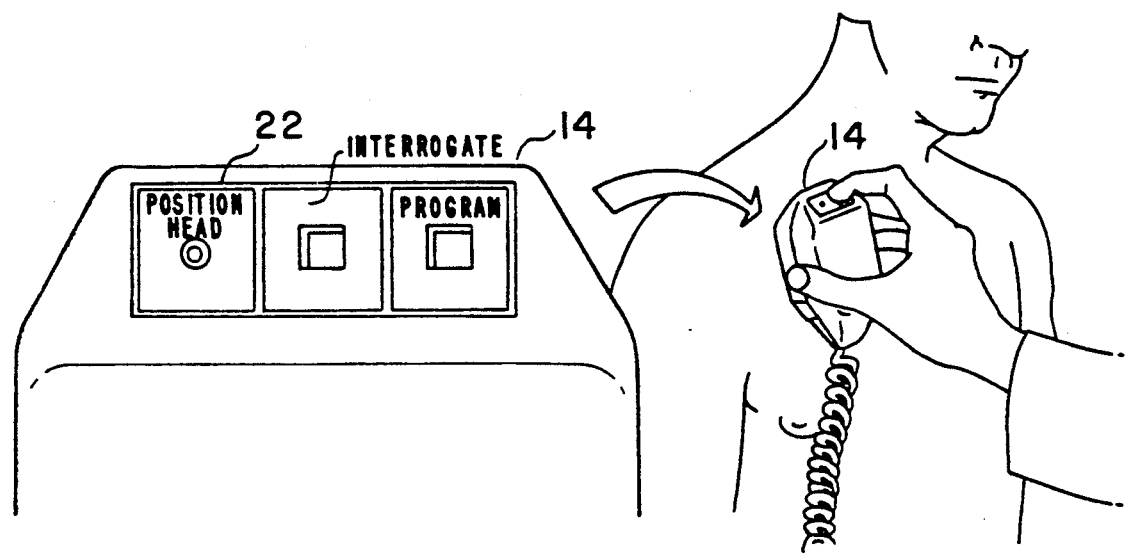
FIG. 3 depicts the positioning of the programming head over the implanted pulse generator and the indicator light LED for indicating proper position for both programming in and telemetry-out from the implanted pulse generator.

As described hereinbefore, the prior art manually adjusted gain control and software implemented automatic gain control was set to the maximum gain during the idle mode to facilitate the early acquisition of the RF uplinked telemetry signal and to minimize the amount of time it took to reposition the programming head 14 in relation to the implanted pulse generator 20 of FIGS. 3 an 4. Unfortunately, at maximum gain, an RF signal could not be distinguished from low level noise as shown in the typical signal depicted in FIG. 7, and time is lost as the user searched for a lower gain valve which can distinguish noise from the telemetry signal.

In the software-implemented, old algorithm shown in U.S. Pat. No. 4,531,523 (FIG. 3), the gain was likewise initialized at maximum and decreased in steps until telemetry signals were differentiated from amplified background noise. The old automatic gain control algorithm was uni-directional in design. On initialization or a major time out (98 ms.), the gain would be set at its highest level and reduced incrementally as noise was detected. The noise detection logic defined noise as two pulses that are not 1's or 0's that occur within 8 ms. This 8 ms. time window was needed to filter out the implantable pulse generator output induced noise and the false errors that are detected at the end of blanking intervals in the implanted pulse generator. This old algorithm could not increase the gain level incrementally, because it had no detection mechanism for bit-level dropouts. It could only detect long signal loss intervals of greater than 98 ms. and would jump back to high gain under this condition. Using this method, the gain would stabilize at a level just below the noise threshold. At this level, occasional noise hits are probable, and if they occur at an interval greater than 8 ms., they will cause uplink message corruption with no subsequent gain adjustment.

The attack and decay characteristics of the old algorithm were slow and inaccurate. On initial programming head positioning, the gain was set at maximum and reduced as fast as noise was detected if that noise recurred at frequency greater than 125 Hz. Rapid reduction was not realized, however, because if the gain was reduced, noise hits became less frequent. The response time of the old algorithm, using a simple head positioning test and a "programmed nominal" function required in regard to certain implantable pulse generator models a 3-5 second settling time to obtain reliable communications. Even after settling, the gain tended to be nearer the maximum gain. This characteristic of the old algorithm is depicted in the top curve of FIG. 9, and it is specifically shown and described in the aforementioned U.S. Pat. No. 4,531,532.

The new automatic gain control and algorithm of the present invention employs linear attack and decay characteristics. Initially, in the "idle" or acquisition mode, the automatic gain control value is set at zero gain and steps through the gain range in a 2 db increment stairstep pattern. When the high gain limit is reached (software selectable), the search starts over at zero gain again. Thus, in the idle mode, the automatic gain control gain value rapidly increases and decreases as shown in the bottom curve of FIG. 9 in the search for a hit on a transmitted RF pulse signal.

Figure 9:
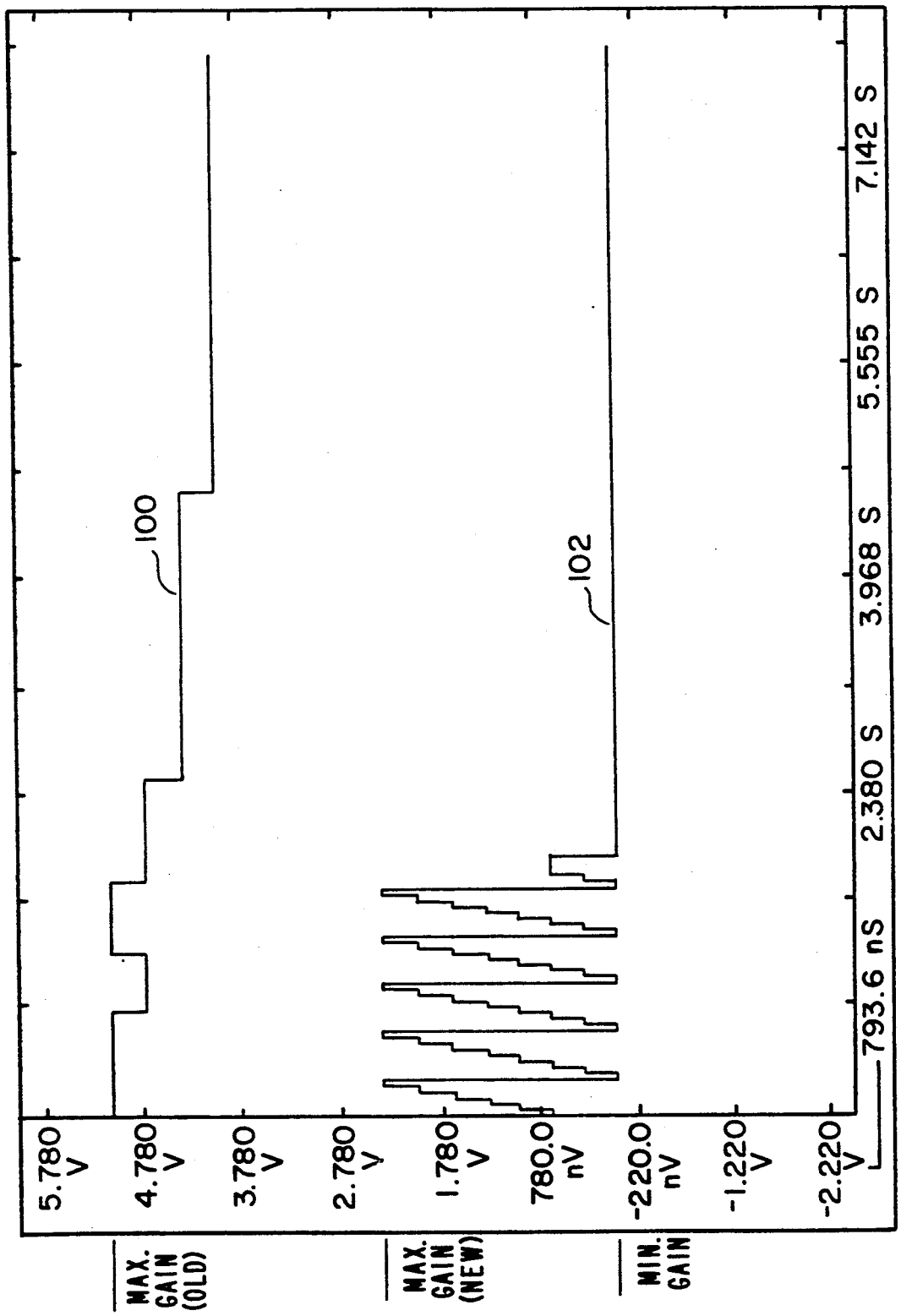
FIG. 9 depicts the step-wise adjustment of gain in accordance with the old and new algorithms.

Turning now to FIG. 10, a first embodiment of the new AGC algorithm of the present invention usable with the bit-based telemetry format is depicted in simplified fashion. In FIG. 10, the program is started upon command of the PPU microprocessor within programmer 10 and in the idle mode, that is, in the absence of any detected RF data or noise signals, the gain cycles between 0 and 7 (maximum) through the loop comprising blocks 70-80. Initially, a 45 ms. timer 72 is started, and if no telemetry signal is sensed within the 45 ms. time period, then the link status flag is set to "BAD" in block 75 and the gain is incremented in block 76 by one step. If no telemetry signal is sensed over a predetermined number of times up to a maximum gain, then decision block 78 commands block 80 to reset the gain to minimum. This sequence is depicted in FIG. 9 in regard to the lower gain curve depicting the behavior of the automatic gain control circuit in the idle mode. As long as the gain is not at its maximum value, the 45 ms. timer is restarted at block 72, and the gain is incremented. The state of the link status flag (BAD or GOOD) is employed in the signal strength algorithm of FIG. 12.

When successive telemetry signals occur within the 45 ms. time period, interrupts are generated in block 82. The intervals between interrupts are measured in block 84 and compared to a further interval of "1 MAX" which exceeds the binary "1" and "0" intervals in decision block 86. If the measured interval is greater than the 1 MAX interval, then the gain is again incremented in block 76. Again the increased gain is compared to the maximum gain in decision block 78 and once maximum gain is reached, the gain is reset to a selectable minimum in block 80.

However, if the measured interval is less than or equal to the maximum binary "1" interval (1.098±15%), then the interval "t" is compared to the interval representing a binary "1" in decision block 88. If the measured interval "t" is equal to a valid "1", then the bit is processed in block 96 and the program loops back to START.

If the measured interval "t" is not equal to a valid "1" but falls between the binary "1" and binary "0" intervals (that is not equal to either the binary "1" or the binary "0" interval plus or minus their respective tolerances) as determined in block 90, then the link status is set BAD in block 92 and the gain is decremented by one step in block 100. But if the measured interval falls within the binary "0" interval as determined in decision block 102, then the gain is neither incremented nor decremented in accordance with the new algorithm. The link status flag is set to "GOOD" in block 94, the "0" bit is processed in block 96 and the program loops back to START.

If the measured interval "t" is determined to be less than a binary "0" interval in block 102, then the link status flag is set BAD in block 92 and the gain is decreased in block 100. In decision block 104, the gain is compared to the minimum gain, and if the decreased gain is less than the minimum gain, then the gain is set to the selectable minimum gain in block 106 and the program loops back to START.

Once a requisite number of sequential data bits are successfully processed in block 96, the uplink telemetry of the data is enabled and the gain is no longer adjusted as the algorithm of FIG. 10 is disabled.

Turning now to FIG. 11, the flow chart of FIG. 10 is modified therein to process frame-based rather than bit based telemetry data. The modification starts at block 84 and loops back to the START block 70 and thus replaces blocks 86–106 of FIG. 10. Again, operating in the idle mode, the algorithm steps through blocks 70–84 of FIG. 10, and if no signal is received in 45 ms., the link status flag is set BAD in block 75 and gain is increased in blocks 76, 78, 80. If a signal is detected within 45 ms. then the interval is measured in block 84 and the measured interval is compared to a 2 ms. interval (greater than the frame length) in decision block 108. If the interval is greater than 2 ms. then the link status flag is set BAD in block 109 and the gain is increased in blocks 110, 112, 114.

If the measured interval is shorter than 2 ms., then the program moves to decision block 116 where the interval is compared to the preset sync interval depicted in FIG. 6. If the sync interval is not matched or is expected in decision block 118, then the program moves to set the link status flag BAD in block 119 and to the decrease gain loop comprising blocks 120, 122 and 124.

However, if the sync interval is matched, the program moves to examine the proper number of intervals between sync intervals in blocks 126, 128 and 130. In block 126, the successive intervals between sync intervals are counted and if two many intervals are detected (more than 5), decision block 128 concludes that the gain is too high and moves to the decrease gain loop starting at block 119. On the other hand, if too many intervals are not detected in decision block 128, then the number of intervals are compared to the expected number in block 130. If too few intervals are detected, then the algorithm concludes that the gain should be increased and moves to the increase gain loop starting with block 109. If, however, the number of intervals is correct, then the status flag is set GOOD in block 132 and the intervals are processed in block 134 and the program loops back to START.

In the decrease gain loop comprising blocks 120, 122 and 124, the gain is decreased in block 120 and compared to the minimum gain in block 122. If the decrease gain is less than the minimum gain, then the gain is set at minimum in block 124.

Similarly, in the increase gain loop comprising blocks 110, 112 and 114, the gain is increased in block 110 and compared to the maximum gain in block 112. If the maximum gain is reached, then the gain is set to minimum in block 114 and the program loops back to start.

To summarize the foregoing, it can be seen that the bit-based and frame-based flow charts and software respond to noise by decreasing gain and to signal drop out by increasing gain during the idle mode, as follows:

|  | Noise | Signal Loss |
|---|---|---|
| bit-based | $0 < t < 1$ or $t < 0$ | $t > 45$ ms. or $t > 1$ max |
| frame-based | $> 5t/\text{frame}$ | $t > 45$ ms. or $t > 2$ ms. |

Where t is the interval between detected 175 kHz RF signals.

When acquisition is achieved, uplink telemetry and storage of the telemetered intervals is enabled for decoding and display. During the uplink telemetry, noise signals may still get through, but the gain will not be changed. In the uplink telemetry mode and in the presence of 175 kHz noise tripping the detect amplitudes, the algorithm measures each interval t, stores successive intervals and continuously sums the stored intervals $t_0$, $t_1$, $t_2$ and compares the sums to the 0 and 1 intervals (in bit-based telemetry). If the sums match a 0 or 1 bit interval, then the uplink is accepted.

Similarly, in frame-based telemetry, successive intervals are stored until the total number of frames ($2 \times 38$) are received. Intervals that are too short to represent a sync interval, dead space interval, or one of the possible ID, LSN or MSN intervals are summed together until a valid interval is detected. Thus, noise signals between the frame-based signals depicted in FIG. 6 are eliminated.

Figure 12:
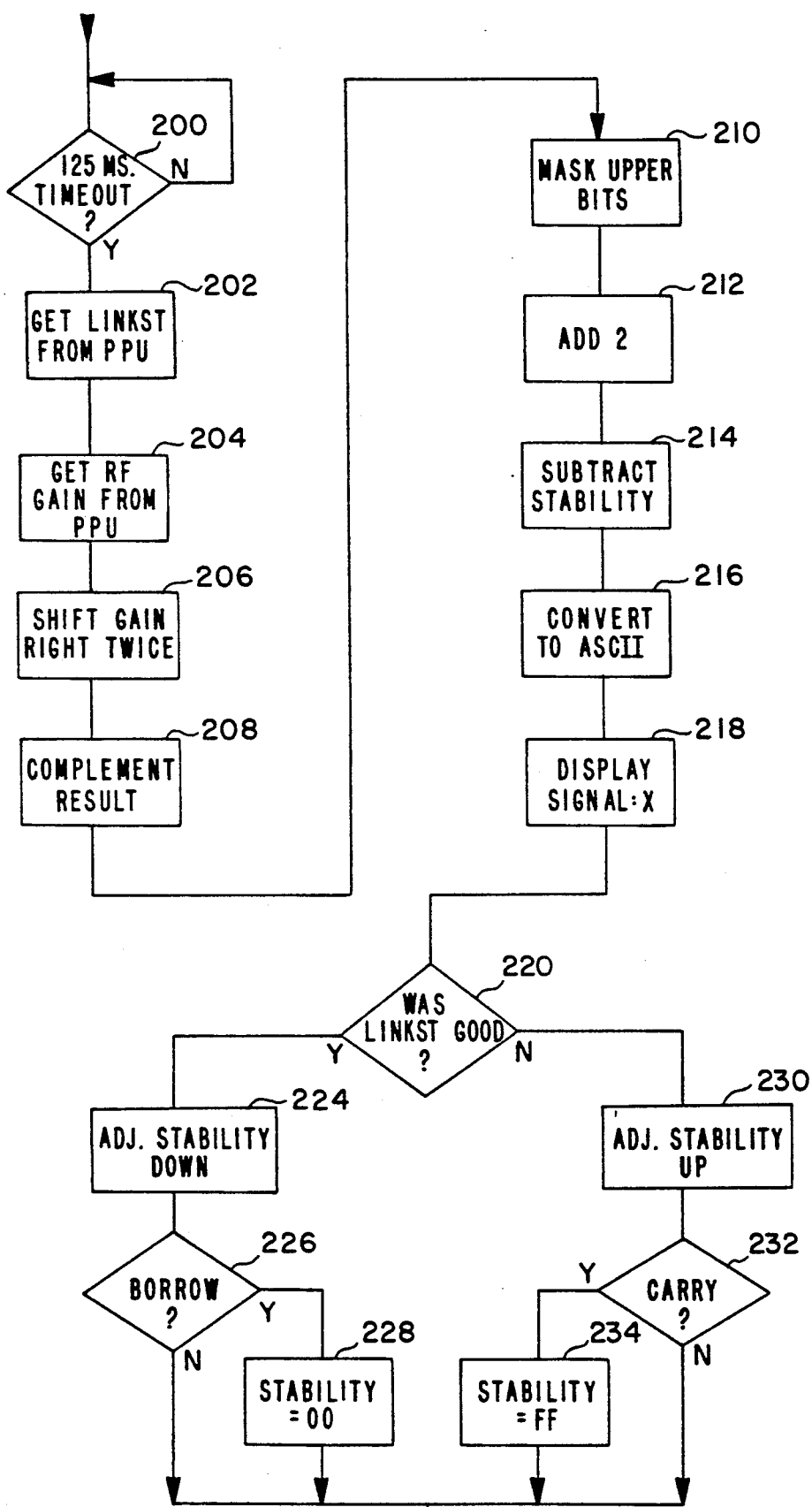
FIG. 12 is a flow chart of the new algorithm for providing the signal strength alphanumeric display.

Turning now to a further aspect of the present invention, to help properly position the programming head during the idle or acquisition mode, the strength of the telemetry signal is indicated to the user employing the algorithms of FIGS. 10 or 11 and FIG. 12 and as set forth in the software listing appended hereto as Appendix A. On the alphanumeric display of the programmer 10, the word "SIGNAL" followed by a value from zero (minimum) to nine (maximum) appears on the left side of the display under "MODE." The value decreases if the signal is interrupted by electrical interference. This information is not available momentarily while the programmer is processing other commands or information. The signal strength algorithm utilizes the real time monitoring of noise or signal drop-out which effects a decrease or increase in the AGC level or value during the idle or acquisition mode, thereby providing real time monitoring of signal integrity and signal-to noise ratio to provide an indication to the user. Since the AGC value is lowest for maximum signal level and highest for minimum level, the value is complemented for use as a signal strength indicator to the user.

In addition to the use of current gain value, a secondary factor is included to provide a stability-of-link factor to the signal strength indication Once every 125 ms. or so, the "GOOD" or "BAD" status of the link is checked. This link status is used to turn off the "position head" LED on the front of the programmer or programmer head. A stability factor is adjusted based on this instantaneous check of link status. The factor is made more negative when the link check status is BAD and more positive when GOOD.

The stability factor is a function of the number of good frames or bits received over time versus the number of bad frames or bits received over a similar period. When the sample of frame status indicates a GOOD bit or frame (block 94 of FIG. 10 or block 132 of FIG. 11), then the stability factor is increased by a fixed value. When the status indicates a BAD bit or frame (blocks 75, 92 of FIG. 10 or 109, 119 of FIG. 11), then the stability factor is reduced by a larger, also fixed value. Once a bad bit or frame is detected, the algorithm requires several consecutive good frames to build the signal indicator value back up to its maximum corresponding with the gain value. Complemented plus 2. If there are a significant number of momentary link instabilities indicated by the stability factor, the resulting signal strength value is reduced, ultimately to 0. If those instabilities diminish, the signal strength level will increase. The maximum displayed signal strength level will then correspond with the complement of the AGC value plus 2 or 9.

The displayed range of signal strength could be artificially adjusted to other values, 0 through 100 for instance, by scaling AGC instability factors accordingly. In the current implementation, the values correspond with AGC levels 0 through 9. The value is displayed on the programmer liquid crystal display and is updated roughly every 125 ms.

When a signal loss occurs, the AGC algorithms scan through gain levels searching for one which will result in valid uplink detection, as described in conjunction with FIGS. 9-11. Without the stability factor in the calculations, the signal strength value would also scan during this time. The stability factor, however, increases negatively at a rapid rate whenever total signal loss occurs. This factor's maximum value corresponds with the maximum AGC value and cancels any AGC level when the link is extremely unstable or nonexistent.

The signal strength feature is desirable, since it allows the physician user to map the optimal position for obtaining a reliable RF signal when the programming head 14 is placed against the patient's chest overlying the implanted pacemaker 20 as depicted in figures 3 and 4. In high noise environments and in cases where the implantable pulse generator 20 implanted in obese patients or is flipped over so that the read switch is further away, it is necessary through trial and error to reposition the programming head and to try different RF signal gain settings as described hereinbefore. The signal level indicator makes the mapping of the location of the implanted pulse generator easier and provides the physician user with a quantitive measure of optimal position.

Although the signal strength indicator has been described hereinbefore as appearing on the LCD screen of the programmer 10, it will be understood that it could as well appear on the programming head 14 as a numeric display for convenience of the physician user. Furthermore, as described hereinbefore, th indicator value could appear on the CRT display of the Model 9760 programming system and/or on both the programming head and the Model 9710 or Model 9760 alphanumeric displays. Furthermore, it will be understood that both the gain value and the signal strength indicator value may be printed out on the printer when a record is made of the telemetry out of the data from the implanted pacemaker.

FIG. 12 illustrates a flow chart of a program implementing the above description of the signal strength calculation algorithm.

In decision block 200, the timeout of the asynchronous timer 15 checked. Upon the timeout of the 125 ms. timer, the MPU get link status from the PPU at block 202 and gets the RF gain value from the PPU at block 204. In block 206 the gain value is shifted right twice. The shifted gain is complemented in block 208.

Block 210 masks the upper bits to prevent a value once complemented from exceeding 7. For example, if the shifted gain is at zero and it is complemented, it will end up being too large a number for the display range of 0 to 9. In block 212, "2" is added to make the minimum displayed value without noise be something other than zero.

At block 214, the previously-calculated stability value is subtracted and the result is converted to ASCII code in block 216. At block 218, the LCD display "signal:—" is created with the blank space filled with the calculated numeric signal strength.

Next, the stability factor is updated. At decision block 220, if the link status flag previously received from the PPU at block 202 is GOOD, the stability value is adjusted down by pre-determined amount.

At decision block 226, if the adjustment at block 224 causes a borrow, the stability factor value at block 228 is limited to zero.

If the result of the link status check at block 220 is bad, then the stability factor is adjusted "up" in block 230 again by a separate pre-determined value. If there is a carry as a result of that operation in block 232, the stability value is limited to a maximum in block 234.

As described earlier, the adjustment values are not equal; preferably the "up" adjustment is a predetermined value substantially greater than the "down" adjustment. The new stability factor is used in block 214 the next time that the process is repeated.

The aforementioned algorithms are implemented in the program listing attached hereto as Appendix A.

The following description explains the expressions appearing in the appended software listing: The Peripheral Processing Unit (PPU) is a separate micro-processor used in the 9710 to process RF bursts transmitted by the IPG. This processor is interrupted each time an RF burst is detected. Under normal situations (not programming the IPG) the PPU is in an "idle" mode. In this mode, interrupts are enabled and the function of the PPU is to adjust the Automatic Gain value to maintain a sufficient signal level for future communications. This Automatic Gain value is outputted to a port of the micro-processor whenever it is changed and controls the gain of the RF amplifier in the Model 9710 in 2 dB steps.

If there is no interrupt for 45 milliseconds, an internal timer times out and the unit TIMEO is called. This unit's major function is to set flags used throughout the system in response to a telemetry gap of 45 msec and to adjust the gain up by one step in an attempt to locate the signal. This assumes that the signal is missing due to lack of gain. If this assumption is false, that is, the signal is missing due to saturation of the amplifier, then the condition will continue until the gain "wraps around" to its minimum value which will eliminate the saturated condition if that is possible.

During idle, if an IPG is present, then the processor is interrupted and control is given to the unit EXTO. The time interval since the last such interrupt is measured. This interval is compared with stored values to check the interval for conformance to the requirement for a sync interval. If the interval is determined to be a valid sync interval, then the number of intervals collected since the last sync interval was received is checked. Under normal circumstances, i.e. correct gain adjustment, there should be 5 intervals in one frame there have been more than this number, then extra noise is indicated and the gain level is adjusted down. If there are less than 5 intervals in the previous frame, then signal loss is indicated and the gain is adjusted up. Since interrupts could be lost due to amplifier saturation, the gain is allowed to wrap around to its minimum value as in the time-out case.

When a valid frame of 5 intervals including sync is detected, EXTO sets a flag to indicate a good frame has been received. If the previous frame is in error then the flag is cleared to indicate this condition as well. This flag is checked once every 125 ms when update of the SIGNAL indicator is required.

During uplink data reception, the PPU is placed in a unique mode which prevents AGC due to timing constraints as well as the undesirability of changing gain level and introducing transients during uplink reception. During this time, collected intervals are stored for later processing once all uplink data has been received. During uplink decoding, if errors are detected, flags are set which are later processed to adjust the gain level for noise or signal loss.

Once the uplink data is received, it is processed by the unit TELEM in conjunction with subordinate units such as GET FRAME and GET_VAL. These subordinate units implement what noise immunity is possible by adding collected intervals and checking each field range. If the current sum is less than the minimum value for the current field, then the next collected interval is added in. If noise was received, two smaller intervals equalling the correct interval would be stored.

The signal indicator is calculated by the Master Processing Unit (MPU). The responsible unit is LNKCHK. This unit interrogates the PPU once every 125 ms and receives the current gain level and last frame status. The gain level is complemented and incremented by 2 to provide a gain floor of 2. This is done to provide a minimum signal gain level with no noise and leave room for noise when the signal level is small. Th gain value is complemented because the actual value used is small for larger signals and large for smaller signals.

Once the gain value has been modified for use by the signal indicator algorithm, a stability factor is calculated. This stability factor is a function of the number of good frames received over time versus the number of bad frames received over a similar period. When the sample of frame status indicates a good frame, then the stability factor is increased by a fixed value. When the status indicates a bad frame then the stability factor is reduced by a larger, also fixed value. Once a bad frame is detected, it requires several consecutive good frames to build the signal indicator value back up to its maximum corresponding with the gain value, complemented, plus 2.

The following designs are included in the appended software:

| PPU: | |
|---|---|
| TIMEO | 45 msec PPU time-out handler |
| EXTO | RF telemetry handler |
| TELEM | uplink processing executive |
| GET_FRAME | subroutine to decode a frame |
| GET_VAL | subroutine to look up data intervals |
| MPU: | |
| LNKCHK | Link status, Signal indicator unit. |

The appended code is generic and not microprocessor dependent. The code which adjusts the gain value is 8051. The code which calculates the signal strength is Z80.

APPENDIX A

```
;---*-/$$$$$$$$$$$$$$$$$$$$$$$$$$$$$$$$$$$$$$$$$$$$$$$$$$$$$$$$$$$$$
;
;
;
;
; 1 TASK TIMEO (TELEMETRY FUNCTION).
;
; 1.1 CALLED BY:
;
;       Hardware timer interrupt 45 msec)
;
; 1.2 DESCRIPTION OF TASK:
;
; The timer  0  interrupt service  routine  is invoked  whenever timer  0
; overflows.  During initialization,  this timer is  loaded with 8ad0h  or
; 35536d.  This  value corresponds with  65536 - (45 ms/1.5 us).  If  no
; telemetry interrupts  occur (see EXTO) prior  to timer  overflow,  this
; routine will be called.  The purpose  of this routine  is to reset  the
; timer, adjust the gain and place the telemetry system in an initialized
; state.
;
; If the PPU is currently awaiting uplink following downlink, then a  flag
; is set while data is being received and no gain correction will occur.
;
; After the reception of data is complete, the flag is cleared and the timer
; is disabled while the received message is processed.
;
```

```
; 1.3 FLOW
;
; 1.3.1 PDL
;
;    -save acc
;     save psw
;     stop timer
;     reset timer to 8ad0h for 45 ms per int [basetime -> th0,tl0]
;     restart timer 0
;     select register bank 2
;     load time registers with ffh [timehi,timelo <-- ffffh]
;     set timeout flag [to_f]
;     clear frame detected flag [frame_f]
;     reset frame counter [frame_cnt=0]
;     reset gain adjustment flag [gain_adj=0]
;
;     if not doing telem [ghold=0]
;         get gain [a=rf]
;         mask off unused bits [a=a & 00111100B]
;         increment gain [a+gain_adj_up]
;         save local copy [rf=a]
;         if > max gain [a=(gain_max+4)]
;             get minimum gain [ a=gain_min]
;             save local copy [rf=a]
;         endif
;
;         save DPTR [push]
;         set DPTR to rf control addr [DPTR=6001H]
;         set gain [@DPTR=a]
;         restore DPTR
;         flag bad link [link_flag=0]
;         reset good frame counter [link_cnt=0]
;     endif
;
;     reset interval (pulse) counter [R6=0]
;     set timeout flag [toflag=1]
;     restore registers [PSW,a]
;     exit interrupt
;
;
; 1.4 CONSTRAINTS
;
;     Preserve used registers.
;
; 1.5 INPUT REQUIREMENTS:
;
; 1.5.1 PROCESSING:
;
;     None assumed.
;
; 1.5.2 DATA ELEMENTS
;
;     rf           RF control (gain) register
;     th0,tl0      timer 0
;     ghold        telemetry waiting for uplink flag
;
```

```
; 1.5.3 EQUATES
;
;    gain_adj_up    04H        ;gain increase increment
;    gain_min       00H        ;Minimum gain value
;    gain_max       1CH        ;Maximum gain value
;    basetime       8AD0H      ;Base timer value
;
;
; 1.6 OUTPUT REQUIREMENTS:
;
;
; 1.6.2 DATA ELEMENTS
;
;    to_f           timeout occurred flag
;    frame_f        frame detected flag
;    frame_cnt      receive frame counter
;    link_flag      telemetry established flag
;    link_cnt       count of consecutive good frames received
;    r6.b2          burst counter (used by ext0)
;    th0            timer 0 high byte
;    tl0            timer 0 low byte
;    rf             RF control register
;    toflag         timeout flag for ext0
;    $6001          MPU interface register
;    gain_adj       gain adjustment needed flag
;
; 1.7 LOCAL DATA
;
;    Register bank 2    r6
;
;
; 1.8 UNIT LEVEL TEST LIST
;
; <test #>   <test case description>   input values      output values
;
;    1.  Timer reset                   ------            th0 = 8AH
;                                                        tL0 = D0H
;                                      ghold=0
;                                      to_f = 0          to_f = 1
;                                      frame_f = ffH     frame_f = 0
;                                      frame_cnt = ffH   frame_cnt = 0
;                                      link_flag = ffH   link_flag = 0
;                                      link_cnt = ffH    link_cnt = 0
;                                      gain_adj=1        gain_adj=0
;                                      r6=2              r6=0
;
;    2.  Gain adjust (normal)          ghold=0
;                                      rf = 0            rf = 04
;
;    3.  Gain adjust (max)             ghold=0
;                                      rf = 1cH          rf = 0
;
;    4.  Telem in progress             a=12h
;                                      psw=18h
;                                      ghold=1
;                                      toflag=0          toflag=1
;                                                        a=12h
;                                                        psw=18h
```

```
;
;
;---++/ $$$$$$$$$$$$$$$$$$$$$$$$$$$$$$$$$$$$$$$$$$$$$$$$$$$$$$$$
;
;

;---**/$$$$$$$$$$$$$$$$$$$$$$$$$$$$$$$$$$$$$$$$$$$$$$$$$$$$$$$$$
;
;
;
; 1 TASK EXT0 (TELEMETRY FUNCTION)
;
; 1.1 CALLED BY:
;
;      Hardware telemetry (RF) interrupt
;
; 1.2 DESCRIPTION OF UNIT:
;
; This task is responsible for servicing telemetry interrupts. These
; interrupts are generated by the detection of RF bursts and represent the
; pulse positions within the telemetry frames.
;
; -- IDLE MODE --
;
; EXT0 operates in two modes. In the first or "IDLE" mode, the routine reads
; and saves the contents of timer 0 and resets timer 0 to a count of 45 msec
; (8AD0H).
;
; The state of the "gain_adj" flag is checked to see if the need for a gain
; adjustment has been detected by GET_FRAME. If set the appropriate
; adjustment code is executed and EXT0 is exited.
;
; If gain_adj is not set, a check is then made to determine if the time value
; is greater than a frame interval (approximately 2 msec). If greater, the
; routine is exited. If this occurs too many times in a row, then the
; condition will be treated the same as missing pulses, the gain will be
; adjusted up.
;
; Next, a check is made to detect the start of frame sync interval (122
; usec). If a sync interval is detected ag FRAME_F is set, the pulse
; counter is set to 1, the frame counter   . LINK_CNTs are incremented and
; the interrupt is exited.
;
; If the time interval is not a sync interval, and a sync was expected the
; RF gain is adjusted up one increment. If a data field was expected the
; interval is saved in the buffer and the interrupt is exited.
;
; During gain adjustments the gain value is allowed to wrap-around to zero
; when maximum gain is reached.
;
; No intervals are saved in IDLE mode. Its purpose is make ajustments in
; gain while no telemetry or markers are being received.
;
; -- RECEIVE MODE --
;
; The second mode is the "RECEIVE" mode of operation. In this mode, the
; routine also reads and saves the contents of timer 0 and resets timer 0 to
; a count of 45 msec (8AD0H).
;
```

```
; In addition, the time interval is placed into a circular buffer pointed to
; by P2 and R1 (initialized by telem).  The buffer pointer (R1) is allowed
; to wrap-around, and may fill the entire page allocated to the buffer
; (3400H) many times during a message sequence.
;
; EXT0 is then exited.
;
; Fast execution during the "receive" mode is critical for the operation of
; the programmer.  A hardware input filter is in place which will allow a
; minimum pulse interval of approximately 60 usec +/- 5%.  To allow
; execution of the upper level or applications code during high noise
; levels, EXT0 must execute faster than 60 usec.  Currently, the execution
; time is estimated at approximately 51 usec (43.5 usec for the code and 7.5
; usec latency time).
;
; Some interval measurement error will exist.  This depends on the
; instruction being executed at the time of the interrupt and may be from 3
; to 9 cycles or 4.5 to 7.5 usec.  The interval measurement code will
; compensate for 4.5 usec of latency giving a measurement accuracy of
; approximately  0 to 3 usec.
;
; 1.3 FLOW
;
; 1.3.1 PDL
;
;     save PSW
;     select register bank 2
;     save acc [r4]
;     stop timer [0]
;     save timer count [timelo, timehi <--- th0,tl0]
;     reset the timer [th0, tl0 <--- 8ad0h]
;     start timer [0]
;
;     if timeout occured [toflag=1]
;         clear timeout flag [toflag]
;         restore acc [r4]
;         restore PSW
;         exit
;     endif
;
;     if telem mode [ghold = 1]
;         time msb to the buffer [@r1 = timehi]
;         bump buffer pointer [r1+1]
;         time lsb to the buffer [@r1 = timelo]
;         bump buffer pointer [r1+1]
;         restore acc [r4]
;         restore PSW
;         exit
;     else
;         if gain adjustment flagged by GET_FRAME [gain_adj=1]
;             if adjustment is up [gain_up=1]
;                 clear adjustment needed flag [gain_adj=0]
;                 adjust gain up [goto GN_UP]
;             else
;                 clear adjustment needed flag [gain_adj=0]
;                 adjust gain down [goto GN_DN]
;             endif
;         else
```

```
;               if last interval before pace [timehi > 90h]
;                   if two intervals > 2 ms in a row [missing_f=1]
;                       reset flag [missing_f=0]
;                       flag link bad [link_flag=0]
;                       reset link counter [link_cnt=0]
;                       adjust gain up [goto GN_UP]
;                   else
;                       set flag for next time [missing_f=1]
;                       set ignore flag [ignoref=1]
;                       clear timeout flag [toflag=0]
;                       restore acc [a=r4]
;                       restore PSW
;                       clear pending interrupt [clr IE0]
;                       exit interrupt
;                   endif
;               else
;                   if interval < Maximum sync time [< sync_max]
;                       set new frame flag [frame_f]
;                       count the new frame [frame_cnt]
;                       save pulse counter value [a=r6]
;                       reset pulse counter [r6=1]
;                       if ignore flag clear [ignoref=0]
;                           if sync expected [a=1 or 6]
;                               bump good frame counter [link_cnt]
;                               if reception threshold reached [link_cnt >= 38]
;                                   reset good frame counter [link_cnt=0]
;                                   restore acc [a=r4]
;                                   restore PSW
;                                   clear pending interrupt [clr, IE0]
;                                   exit interrupt
;                               endif
;                               show good link [link_flag=ff]
;                           else
;                               if missing pulses [a < 6]
;                                   if no gain adjust flagged [waitf=1]
;                                       clear flag [0 --> waitf]
;                                       exit interrupt [goto XX3]
;                                   else
;                                       reset link flag [link_flag=0]
;                                       reset good frame counter [link_cnt=0]
;                                       adjust gain up [goto GN_UP]
;                                   endif
;                               endif
;                           endif
;                       else
;                           if sync expected [r6 = 6]
;                               set gain wait flag [waitf=1]
;                               clear pulse counter [r6=0]
;                               reset link flag [link_flag=0]
;                               reset good frame counter [link_cnt=0]
;                               adjust gain down [goto GN_DN]
;                           endif
;                       endif
;                   endif
;               endif
;           endif
;       endif
;
```

```
; XX3:
;     restore acc [a=r4]
;     restore PSW
;     clear pending interrupt [clr IE0]
;     exit interrupt
;
; GN_UP:
;     get gain value [a=rf]
;     isolate gain [a & 3ch]
;     bump gain [a+gain_adj_up]
;     if gain > max gain [a > gain_max]
;         set gain to minimum [a=gain_min]
;     endif
;     save copy of
 gain value
;  .  save dptr [dph,dpl]
;     set rf control address [dptr=6001h]
;     write rf control register [@dptr=a]
;     restore dptr[dph,dpl]
;     restore acc [a=r4]
;     restore PSW
;     clear pending interrupt [clr IE0]
;     exit interrupt
;
; GN_DN:
;     get gain value [a=rf]
;     isolate gain [a & 3ch]
;     dec gain [a-gain_adj_dn]
;     if gain < min gain [carry=1]
;         set gain to zero [a=gain_min]
;     endif
;     save copy of gain value [rf=a]
;     save dptr [dph,dpl]
;     set rf control address [dptr=6001h]
;     write rf control register [@dptr=a]
;     restore dptr[dph,dpl]
;     restore acc [a=r4]
;     restore PSW
;     clear pending interrupt [clr IE0]
;     exit interrupt
;
;
; NOTE: GN_UP and GN_DN are tested during the unit testing of EXT0. No
; individual tests are executed for these (dedicated) sections of code.
;
;
; 1.4 CONSTRAINTS
;
; Execution time must be < 58 microseconds for processing the pframe pulse
; to avoid an overrun condition (pframe to psync).
;
; RF burst occurring at an interval < 100 usec are filtered out by a
; one-shot in the hardware. Therefore noise pulses may mask the reception
; of valid data pulses.
;
; The circular buffer used by EXT0 for interval storage MUST be limited to
; 256 bytes. This allows automatic buffer wrap-around while storing data in
; the buffer through P2. Buffer wrap is accomplished by allowing the
; indirect address (LSB) in R1 to roll.
```

```
;
; The high level routine will be removing the data from this buffer at an
; average rate equal to the storage speed due to the low duty cycle of the
; frames (5 pulses in 2 msec.).
;
;
; 1.5 INPUT REQUIREMENTS:
;
; 1.5.1 PROCESSING:
;
; 1.5.2 DATA ELEMENTS
;
;       r4.b2              accumulator save
;       r6.b2              pulse counter
;       r1.b2              interval buffer pointer
;       timehi             interval timer
;       timelo             interval timer LSB
;     - frame_f            new frame flag
;       frame_cnt          frame counter
;       link_cnt           number of consecutive good frames count
;       waitf              don't adjust gain flag
;       ghold              telemetry in progress flag
;       toflag             interval timeout flag
;       rf                 copy of rf control register
;       gain_adj           gain adjustment required flag
;       gain_up            gain up/down flag
;       sy_max             equate defining the max sync interval [8b28]
;
; 1.6 OUTPUT REQUIREMENTS:
;
; 1.6.1 PROCESSING
;
; 1.6.2 DATA ELEMENTS
;
;       toflag             timeout occurred flag
;       link_flag          communications established flag
;       $3400              time interval buffer
;       $6001              rf control register
;       IE0                interrupt control flag
;       missing_f          flag indicating interval > 2ms
;
; 1.7 LOCAL DATA
;
;       Register bank 2    r1,r6,r4
;
;
; 1.8 UNIT LEVEL TEST LIST
;
;       <test case description>        input values    output values
;
;       Telem mode, no timeout.        a = AAH
;                                      PSW = bank 1    $3402 = 12H
;                                      toflag = 0      $3403 = 34H
;                                      th0,tlo=1234h   r1 = 4
;                                      P2 = 34H        a = AAH
;                                      r1=02           PSW = bank 1
;
```

```
;       Telem mode, timeout.                    a = AAH         a = AAH
;                                               PSW = bank 1    PSW = bank 1
;                                               toflag = 1      toflag = 0
;
;
;       Idle mode, no gain adjust flagged,
;       timer 0 overflow.                       ghold=0
;                                               gain_adj=0
;                                               TF0=1
;                                               timehi=91H
;                                               missing_f=1
;                                               rf=04           rf=4
;
;
;
;       Idle mode, time interval >
;       2 msec.                                 a = AAH         a = AAH
;                                               PSW = bank 1    PSW = bank 1
;                                               th0,tl0=9100h   ignoref=1
;                                               ignoref=0
;
;       Idle mode, sync detected, sync          th0,tl0=8a26h
;       expected (r6=1), ignore flag set.       frame_f=0       frame_f=0
;                                               gain_adj=0
;                                               r6=1
;                                               frame_cnt=1     frame_cnt=2
;                                               ignoref=1
;                                               link_cnt=1      link_cnt=1
;
;       Idle mode, sync detected,               th0,tl0=8a26h
;       sync expected (r6=1), reception         frame_f=0       frame_f=1
;       threshold not reached, ignore           frame_cnt=1     frame_cnt=2
;       flag clear.                             r6=1
;                                               gain_adj=0
;                                               ignoref=0
;                                               link_cnt=1      link_cnt=2
;                                               link_flag=0     link_flag=0
;
;       Idle mode, sync detected,               th0,tl0=8a26h
;       sync expected (r6=1), reception         frame_f=0       frame_f=1
;       threshold reached,                      frame_cnt=1     frame_cnt=2
;       link bad, ignore flag clear.            r6=1            r6=1
;                                               gain_adj=0
;                                               ignoref=0
;                                               link_cnt=37H    link_cnt=0
;                                               link_flag=0     link_flag=ffh
;
;       Idle mode, sync detected,               th0,tl0=8a26h
;       sync expected (r6=1), reception         frame_f=0       frame_f=1
;       threshold reached,                      frame_cnt=1     frame_cnt=2
;       link good, ignore flag clear.           r6=1            r6=1
;                                               gain_adj=0
;                                               ignoref=0
;                                               link_cnt=37H    link_cnt=0
;                                               link_flag=ffh   link_flag=ffh
;
;       Idle mode, sync detected,               th0,tl0=8a26h
;       sync expected (r6=1), reception         frame_f=0       frame_f=1
;       threshold reached,                      frame_cnt=1     frame_cnt=2
```

```
;      ignore flag clear.              r6=1
;                                      gain_adj=0
;                                      ignoref=0
;                                      link_cnt=37H    link_cnt=0
;                                      link_flag=0     link_flag=ffh
;
;
;      Idle mode, sync detected,       th0,tl0=8a26h
;      sync expected (r6=6), reception frame_f=0       frame_f=1
;      threshold not reached, ignore   frame_cnt=1     frame_cnt=2
;      flag clear.                     r6=6
;                                      gain_adj=0
;                                      ignoref=0
;                                      link_cnt=1      link_cnt=2
;                                      link_flag=0     link_flag=0
;
;      Idle mode, sync detected,       th0,tl0=8a26h
;      sync expected (r6=6), reception,frame_f=0       frame_f=1
;      threshold reached, ignore       frame_cnt=1     frame_cnt=2
;      flag clear.                     r6=6
;                                      gain_adj=0
;                                      ignoref=0
;                                      link_cnt=37H    link_cnt=0
;                                      link_flag=0     link_flag=ffh
;
;
;      Idle mode, Sync when not expected, th0,tl0=8a26h
;      gain not max, wait flag clear.  r6=4            r6=1
;                                      gain_adj=0
;                                      $6001=0         $6001=8
;                                      rf=4            rf=8
;                                      link_flag=ffH   link_flag=0
;                                      waitf=0         waitf=0
;
;      Idle mode, Sync when not expected, th0,tl0=8a26h
;      gain max, wait flag clear.      r6=4            r6=1
;                                      gain_adj=0
;                                      $6001=3Ch       $6001=0
;                                      rf=1CH          rf=0
;                                      link_flag=ffH   link_flag=0
;                                      waitf=0         waitf=0
;
;      Idle mode, Sync when not expected, th0,tl0=8a26h
;      wait flag set.                  a=3
;                                      gain_adj=0
;                                      psw=bank 3      a=3
;                                      IE0 = 1         psw=bank 3
;                                      r6=4            IE0 = 0
;                                      waitf=1         waitf=0
;
;      Idle mode, no sync when
;      expected, gain not min.         th0,tl0=8a30h
;                                      gain_adj=0
;                                      r6=6            r6=0
;                                      waitf=0         waitf=1
;                                      rf=08           rf=04
;                                      $6001=0         $6001=4
;                                      link_cnt=1      link_cnt=0
;                                      link_flag=ffh   link_flag=0
```

```
;    Idle mode no sync when expected,        th0,tl0=8a30h
;    gain min.                               r6=6            r6=0
;                                            gain_adj=0
;                                            waitf=0         waitf=1
;                                            rf=00           rf=00
;                                            link_cnt=1      link_cnt=0
;                                            link_flag=ffh   link_flag=0
;
;    Gain_adj flag set, gain up.             ghold=0
;                                            gain_adj=1
;                                            gain_up=1       STOP:GN_UP
;
;    Gain_adj flag set, gain down.           ghold=0
;                                            gain_adj=1
;                                            gain_up=0       STOP:GN_DN
;
;
;
;
; 1.9 UNIT LIST
;
;    None.
;
;
;---++/ SSSSSSSSSSSSSSSSSSSSSSSSSSSSSSSSSSSSSSSSSSSSSSSSSSSSSSS
;

;
;              EQUATES
;

INTERR    EQU    9                   ;INTERRUPT OVERHEAD ERROR (13.5 usec)

LSN_MIN   EQU    (717*2)/3           ;MIN LSN FIELD TIME
LSN_MAX   EQU    (1204*2)/3          ;MAX LSN FIELD TIME
MSN_MIN   EQU    (1327*2)/3          ;MIN MSN FIELD TIME
MSN_MAX   EQU    (1814*2)/3          ;MAX MSN FIELD TIME

INTBUFF   EQU    3500H               ;TELEM'S INTERVAL BUFFER ADDRESS
ISRBUFF   EQU    3400H               ;ISR'S INTERVAL BUFFER
DBUFF     EQU    3300H               ;DATA BUFFER ADDRESS

MEAS_TOL  EQU    ((15*2)/3)          ;ALLOWABLE MEASUREMENT ERROR
SKEW      EQU    30                  ;TIME INTERVAL WINDOW
BS        EQU    ((SKEW*2)/3)/2      ;SKEW TO CENTER OF FIRST BIT
SYNCTIME  EQU    (122*2)/3           ;SYNC INTERVAL
IDTIME    EQU    (((274-122)*2)/3)   ;TIME TO CENTER OF ID 0

SYNC_MIN  EQU    880EH               ;MIN SYNC INTERVAL
SYNC_AVE  EQU    8818H
SYNC_MAX  EQU    8822H
ID0_MIN   EQU    8B25H  (adjusted +2 for id compensation)
ID0_AVE   EQU    882FH  (adjusted +2 for id compensation)
ID0_MAX   EQU    8839H  (adjusted +2 for id compensation)
ID4_MIN   EQU    8874H
ID4_MAX   EQU    8888H
```

```
;min sync = 8ad0h + 122 - 15.26 - 13.5 = 8b0eh
;max sync = 8ad0h + 122 + 15.26 - 13.5 = 8b22h
;min 0 = 8ad0h + 152.5 - 15.26 - 13.5 = 8b23h
;max 0 = 8ad0h + 152.5 + 15.26 - 13.5 = 8b37h
;min 1 = 8ad0h + 152.5 + 15.26 - 13.5 = 8b38h
;min 4 = 8ad0h + 152.5 + 4 * 30.52 - 15.26 - 13.5 = 8b74h
;max 4 = min 4 + 30.5 us = 8b88h
;

MAX_TIME EQU   0-(1900/8)        ;MAX TIMEOUT COUNT (8 MSEC/COUNT)

SKIP
;---**/SSSSSSSSSSSSSSSSSSSSSSSSSSSSSSSSSSSSSSSSSSSSSSSSSSSSSSSSSSSSSSSSSSSSSS
;
;
; 1 TELEM   (XMIT TASK)
;
; 1.1 CALLED BY:
;
;-    XMIT TASK
;
; 1.2 DESCRIPTION OF UNIT:
;
; This task is called from XMIT when telemetry data is expected following
; a downlink.
;
; The task begins by initializing the data collection (telem) mode of the
; ISR (EXT0) and setting the ghold flag.
;
; Register R1 is used to determine when a new interval is placed into the
; interval buffer at $3400. As intervals are stored, a search is made to
; detect a sync interval. When a sync is found the next interval is
; examined. If this interval is a sync interval or (ID field) is not a
; zero, the routine returns to its sync scanning mode. If a sync followed
; by a zero ID is found, data interval storage is begun.
;
; Data intervals are placed into the interval buffer ($3400) by the ISR and
; are extracted from this circular buffer by telem and placed into more
; permanent storage beginning at $3500. When the intervals are moved the
; values are normalized and corrected for software overhead error.
;
; As the data intervals are moved telem looks for a timeout or buffer full
; condition. When either is encountered, interval storage is stopped and
; the translation phase is begun.
;
; During the interval collection a 1900 msec timer (icg_time) is used to time
; the response from the IPG. This timer is used to halt data collection if
; noise pulses are being received at a rate < 45 msec.
;
; The translation phase involves calls to unit GET_FRAME which decodes the
; intervals stored at $3500 and returns these values to telem. During
; translation SYNC and ID field errors are ignored.
;
; When all 76 data bytes have been translated, the two halves of the message
```

; are compared and, if equal, the message is sent to the MPU.  If an error
; is detected, an error code is returned to the MPU.
;
;
; 1.2.1 GET_FRAME UNIT
;
; The GET_FRAME unit is called after all frames of data have been input (by
; EXT0).  GET_FRAME decodes the pulse interval values placed into the input
; buffer and passes the value of the frame ID and data back to the caller.
; Status, ID value and data will be passed to the calling routine through
; variables fr_stat, fr_id and fr_data.
;
; 1.3 FLOW
;
; 1.3.1 PDL
;
;     clear acc
;     clear timeout count [to_cnt=0]
;     disable interrupts [EA]
;     clear no mans land counter [NO_MAN_HI,LO]
;     select register bank 2
;     clear circular buffer pointers [r0,r1]
;     initialize P2 [p2=msb of isrbuff]
;     clear timeout flag [to_f]
;     enable interrupts [EA]
;     initialize destination pointer [dptr=intbuff]
;     set telemetry receive mode [ghold=1]
;     initialize message timer [icg_time=max_time]
;     save copy of isr buffer pointer [int_ent=r1]
;
; SY1:                         (Wait for sync interval)
;     while isr pointer unchanged [int_ent=r1]
;         if timer expired [icg_time = 0]
;             flag error [err_byt=ffH]
;             set num of bytes to mpu [a=1]
;             go complete request [EXIT_COM]
;         endif
;     endwhile
;
;     put in telem buffer  [call mov_int]
;     bump pointer to next interval [r0+2]
;
; CHECK_SYNC:                  (Check interval for sync)
;     get interval [@r0]
;     if msb of interval not = sync [high sync_ave]
;         bump source pointer [r0+2]
;         bump saved pointer to next [int_ent +2]
;         reset data pointer [dptr=intbuff]
;         goto SY1
;     endif
;     if lsb of interval not = sync [low sync_ave]
;         bump saved pointer to next [int_ent +2]
;         reset data pointer [dptr=intbuff]
;         goto SY1
;     endif
;     bump saved pointer to next [int_ent +2]
;

```
; ID_WT:                    (Wait for ID of 0)
;     while isr pointer unchanged [int_cnt=r1]
;         if timer expired [igc_time = 0]
;             flag error [err_byt=ffH]
;             set num of bytes to mpu [a=1]
;             go complete request [EXIT_COM]
;         endif
;     endwhile
;     put in telem buffer [call mov_int]
;     if interval = ID of zero or 4 [@r0 < id1_min or id3_max<@r0<id5_min]
;         go wait for data [data_wait]
;     else
;         bump no mans count [NO_MAN_HI,LO +1 (16 bit)]
;         if no mans count reached [NO_MAN_HI = 4]
;             goto NOMAN_ERR
;         endif
;         point back to start of interval [r0-2]
;         go check for sync [goto CHECK_SYNC]
;     endif
;
; DATA_WAIT:                 (Wait for message to be received)
;     bump saved pointer to next [int_cnt+2]
; DW1:
;     while isr pointer unchanged [int_cnt=r1]
;         if timer expired or 45 msec timeout or buffer full
;                         [igc_time = 0, to_f=1, dph = 39H]
;             go process intervals [COLLECT]
;         endif
;     endwhile
;     get interval msb from isr buffer [@r0]
;   - put in telem buffer  [call mov_int]
;     bump pointer to next interval [r0+1]
;     bump saved pointer to next [int_cnt +2]
;     goto DW1
;
; COLLECT:                   (Process collected intervals)
;     turn MPU interrupt off [EX1]
;     turn telemetry interrupt off [EX0]
;     clear telem flag [ghold]
;     turn timer interrupt off [ET0]
;     stop the timer [TR0]
;     select register bank 2
;     prevent gain adjust following decode [waitf=1]
;     reset interval counter [r6=0]
;     select register bank 1
;     init loop counter [frm_cnt=76]
;     init destination pointer [dptr = dbuff]
;     init source pointer save [bphi,bplo = intbuff]
;
;     do: (DATA_DO)
;         get frame ID and data [GET_FRAME]
;         dec frame counter [frm_cnt-1]
;         if frame status bad [(fr_stat & 10110100B) <> 0]
;             go report error [FR_ERR]
;         endif
;         save data [@dptr=fr_data]
;         bump pointer [dptr+1]
;     while (frm_cnt > 0)
```

```
; COMPARE:                    (Compare message halves)
;    get message length [frm_cnt=38]
;    set pointer to start of data buffer [dptr=dbuff]
;    set p2 to page address [p2=high dbuff]
;    set r0 to LSB of second half of message [r0=low dbuff +39]
;
;    do: (COMP_DO)
;        get message byte first half [a=@dptr]
;        if halves not equal (a <> @r0)
;            flag error [err_byt=88h]
;            set completion byte count [r4=1]
;            go exit [EXIT_COM]
;        endif
;        decrement counter [frm_cnt-1]
;        bump pointers [dptr+1,r0+1]
;    while (buffer counter <= 0) [frm_cnt]
;
;    (NORMAL COMPLETION)
;    show good completion [err_byt=0]
;    set message length [r4=39]
;
; EXIT_COM:                    (Cleanup and exit)
;    enable gain adjustment [ghold=0]
;    select bank 1
;    reset isr buffer pointer [p2=high dbuff,r0=0]
;    select register bank 0
;    save completion count [r4=a]
;    turn timer on [TR0=1]
;    turn timer interrupt on [ET0]
;    enable telem interrupt [EX0]
;    enable MPU interrupt [EX1]
;    exit [ret_err]
;
; NOMAN_ERR:
;    set completion code [err_byt=fdH]
;    set completion count [a=1]
;    go to common code [EXIT_COM]
;
; FR_ERR:
;    set completion code [err_byt=feH]
;    set completion count [a=1]
;    go to common code [EXIT_COM]
;
; MOV_INT:
;    get msb [a=@r0]
;    save msb of interval [tac_hi=a]
;    bump source pointer [r0+1]
;    get lsb of interval [a=@r0]
;    bump pointer [a=@r0]
;    clear carry
;    compute normalized value lsb [a = a - low(basetime - interr)]
;    save lsb [tac_lo =a]
;    point back to msb [r0-1]
;    get msb [a=tac_hi]
;    compute normalized value msb [a = a - high(basetime - interr)]
;    save value [@dptr=a]
;    bump destination pointer [dptr+1]
```

```
;       get lsb [a=tac_lo]
;       save in buffer [@dptr=a]
;       bump destination pointer [dptr+1]
;       restore a with msb [a=@r0]
;       return to caller [ret]
;
;
;
; 1.4 CONSTRAINTS
;
; This routine must not destroy register (bank 2) data used by ext0.
;
; While searching for the start of uplink at the beginning of this task
; the SYNC and ID fields should be tested as intervals.  Hardware test
; information shows that these fields are more accurately measured by
; individual intervals instead of summing relative to Pframe.
;
;
; 1.5 INPUT REQUIREMENTS:
;
; 1.5.1 PROCESSING:
;
; The interrupt processor (EXT0) must place data frame intervals into
; the buffer before or during the execution of this task.
;
; 1.5.2 DATA ELEMENTS
;
;
;       igc_time           input response timer
;       fr_stat            from GET_BYTE - operation status
;       fr_id              from GET_BYTE - frame ID
;       fr_data            from GET_BYTE - frame data
;       P2                 used by telem isr and this task as buffer pointer
;       r1                 telem isr circular buffer pointer (lsb)
;       bphi,bplo          buffer pointer used by GET_FRAME
;
;
; 1.6 OUTPUT REQUIREMENTS:
;
;
; 1.6.2 DATA ELEMENTS
;
;       $3400              address of telem circular interval buffer
;       $3500              interval buffer used by this task
;       $3300              message buffer (assembled message)
;       ghold              telem mode flag
;       err_byt            task completion code
;       r4.b0              completion data byte count
;       bphi               GET_FRAME interval buffer pointer MSB
;       bplo               GET_FRAME interval buffer pointer LSB
;       ex0                EXT0 interrupt enable
;       ex1                EXT1 interrupt enable
;       et0                Timer 0 interrupt enable
;       tr0                Timer 0 start/stop
;       waitf              Gain (EXT0) wait flag
;       frm_cnt            Input frame counter
;       r6.b2              EXT0 pulse counter
```

```
;       tac_hi              temp valiable
;       tac_lo              temp variable
;
; 1.7 LOCAL DATA
;
;       NO_MAN_HI           no man's land counter hi
;       NO_MAN_LO           no man's counter lsb
;       cmp_cnt             frame counter
;       frm_cnt             frame counter (compare)
;       igc_time            8 msec timer decremented by ROM code
;       dptr                misc pointer
;
;
; 1.8 UNIT LEVEL TEST LIST
;
;       <test case description>      input values       output values
;
;       Initialization and completion.  a=ffh           a=0
;                                       cmp_cnt=aah     cmp_cnt=0
;                                       bank1.r0=55h    bank1.r0=0
;                                       bank1.r1=33h    bank1.r1=0
;                                       icg_time=ffh    icg_time=0
;                                       int_cnt=ffh     int_cnt=0
;
;       Input timer expiration and
;       completion (sync detect phase 1).   start: SY1
;                                           err_byt=0
;                                           bank1.r1=1      err_byt=ffh
;                                           bank1.r0=1      bank1.r4=1
;                                           igc_time=0      tr0=1
;                                           tr0=0           et0=1
;                                           et0=0           p2=34H
;                                           bank 2          bank1.r0=0
;                                           p2=ffh          bank1.r1=0
;                                           bank1.r4=5      bank1.r4=1
;                                           ghold=1         ghold=0
;                                           ex0=0           ex0=1
;
;       Extract and identify invalid MSB    Start:SY1
;       (high) sync interval                p2=34h
;                                           bank1.r1=2      int_cnt=2
;                                           bank1.r0=0      dptr=3500H
;                                           int_cnt=0       End:SY1
;                                           $3400=8c1bH
;                                           icg_time=f0H
;                                           dptr=35ffH
;
;       Extract and identify invalid MSB    Start:SY1
;       (low) sync interval                 p2=34h
;                                           bank1.r1=2      int_cnt=2
;                                           bank1.r0=0      dptr=3500H
;                                           int_cnt=0       End:SY1
;                                           $3400=8a1bH
;                                           icg_time=f0H
;                                           dptr=35ffH
;
;       Extract and identify invalid (LSB)  Start:SY1
;       sync interval (low)                 p2=34h
```

```
                                    bank1.r1=2      int_ent=2
                                    bank1.r0=0      dptr=3500H
                                    int_ent=0       End:SY1
                                    $3400=8b11H
                                    icg_time=f0H
                                    dptr=35ffH ; Extract and identify invalid (LSB)  Start:SY1
; sync interval (high)                p2=34h
                                      bank1.r1=2    int_ent=2
                                      bank1.r0=0    dptr=3500H
                                      int_ent=0     End:SY1
                                      $3400=8b25H
                                      icg_time=f0H
                                      dptr=35ffH ; Extract and identify valid          Start:SY1
; sync interval                       p2=34h
                                      bank1.r1=2    int_ent=2
                                      bank1.r0=0    dptr=3502H
                                      int_ent=0     bank1.r0=2
                                      $3400=8b1bH
                                      icg_time=f0H
                                      dptr=35ffH    End:ID_VT ; Input timer expiration and
; completion (ID 0 detect phase 1).   start: ID_VT
                                      err_byt=0
                                      bank1.r1=1    err_byt=ffh
                                      bank1.r0=1    bank1.r4=1
                                      igc_time=0    End:EXIT_COM ; Extract and identify invalid (MSB)  Start:ID_VT
; ID interval (low)                   p2=34h
                                      bank1.r1=2    int_ent=2
                                      bank1.r0=0    dptr=3500H
                                      int_ent=0     End:SY1
                                      $3400=8c23H
                                      icg_time=f0H
                                      dptr=35ffH ; Extract and identify invalid (MSB)  Start:ID_VT
; ID interval (high)                  p2=34h
                                      bank1.r1=2    int_ent=2
                                      bank1.r0=0    dptr=3500H
                                      int_ent=0     End:SY1
                                      $3400=8c36H
                                      icg_time=f0H
                                      dptr=35ffH ; Extract and identify invalid (LSB)  Start:ID_VT
; ID interval                         p2=34h
                                      bank1.r1=2    int_ent=2
                                      bank1.r0=0    dptr=3500H
                                      int_ent=0     End:SY1
                                      $3400=8b22H
                                      icg_time=f0H
                                      dptr=35ffH
```

```
;
;   Extract and identify valid        Start:ID_VT
;   ID (0) interval                   p2=34h
;                                     bank1.r1=2      int_cnt=2
;                                     bank1.r0=0      dptr=3502H
;                                     int_cnt=0       bank1.r0=2
;                                     $3400=8b23H
;                                     icg_time=f0H
;                                     dptr=35ffH      End:DW1
;
;   Extract and identify invalid (LSB) Start:ID_VT
;   ID interval no mans count not     cmp_cnt=1
;   expired.                          p2=34h          cmp_cnt=2
;                                     bank1.r1=2      int_cnt=2
;                                     bank1.r0=0      dptr=3500H
;                                     int_cnt=0       End:SY1
;                                     $3400=8b22H
;                                     icg_time=f0H
;                                     dptr=35ffH
;
;   Extract and identify invalid (LSB) Start:ID_VT
;   ID interval no mans count         cmp_cnt = feH   err_byt=fdH
;   expired.                          p2=34h          a=1
;                                     bank1.r1=2      int_cnt=2
;                                     bank1.r0=0      dptr=3500H
;                                     int_cnt=0       End:EXIT_COM
;                                     $3400=8b22H
;                                     icg_time=f0H
;                                     dptr=35ffH
;
;   Response timeout (phase 2)        Start:DW1
;                                     to_f=0
;                                     dph=35H
;                                     icg_time=0      End:COLLECT
;
;   45 msec timeout (phase 2)         Start:DW1
;                                     to_f=1
;                                     dph=35H
;                                     icg_time=f0H    End:COLLECT
;
;   Buffer overflow (phase 2)         Start:DW1
;                                     to_f=0
;                                     dph=39H
;                                     icg_time=f0H    End:COLLECT
;
;   Initialize loop.                  Start:DATA_DO
;                                     ghold=1         ghold=0
;                                     et0=1           et0=0
;                                     tr0=1           tr0=0
;                                     bank 1          bank 2
;                                     frm_cnt=0       frm_cnt=76
;                                     dptr=0          dptr=3300H
;                                     bphi=0          bphi=35H
;                                     bplo=ffh        bplo=0
;                                                     End:DATA_DO
;
;   Data loop - count expired.        Start:DATA_DO
;                                     Patch out:GET_FRAME
```

```
;                                        frm_cnt=1      frm_cnt=0
;                                        fr_stat=0      End:COMPARE
;
;       Data loop - normal pass.         Start:DATA_DO
;                                        Patch out:GET_FRAME
;                                        frm_cnt=2      frm_cnt=1
;                                        dptr=3300H     dptr=3301H
;                                        $3300=0
;                                        fr_data=aaH    $3300=aaH
;                                        fr_stat=0      End:DATA_DO
;
;       Data loop - bad frame status.    Start:DATA_DO
;                                        Patch out:GET_FRAME
;                                        frm_cnt=2      frm_cnt=1
;                                        dptr=3300H     dptr=3301H
;                                        $3300=0
;                                        fr_data=aaH    $3300=00H
;                                        err_byt=0      err_byt=feH
;                                        fr_stat=80h    acc=1
;                                                       End:EXIT_COM
;
;       Compare initialization.          Start:COMPARE
;                                        frm_cnt=0      frm_cnt=38
;                                        dptr=0         dptr=3300H
;                                        p2=0           p2=33H
;                                        r0=0           r0=38
;                                                       End:COMP_DO
;
;       Compare good - end of buffer     Start:COMP_DO
;       normal completion.               frm_cnt=1      frm_cnt=0
;                                        dptr=3300H     dptr=3301H
;                                        p2=33H         p2=33H
;                                        r0=26          r0=27
;                                        $3300=12
;                                        $3326=12
;                                        err_byt=ffH    err_byt=0
;                                        a=0            a=39
;                                                       End:EXIT_COM
;
;
; 1.9 UNIT LIST
;
; .  GET_BYTE
;
;.
;
;---++/ $$$$$$$$$$$$$$$$$$$$$$$$$$$$$$$$$$$$$$$$$$$$$$$$$$$$$$$$$$$$$$$$$$$$$

SKIP
;---**/$$$$$$$$$$$$$$$$$$$$$$$$$$$$$$$$$$$$$$$$$$$$$$$$$$$$$$$$$$$$$$$$$$$$$
;
;
; 1 GET_FRAME UNIT   (TELEM TASK)
;
```

; 1.1 CALLED BY:
;
;       TELEM TASK
;
; 1.2 DESCRIPTION OF UNIT:
;
; This unit is used to decode incomming uplink telemetry time intervals and
; assemble data frames.
;
; The buffer pointer for GET_FRAME (bphi, bplo) is initialized to the start
; of the interval buffer by the calling routine. Calls to this unit will
; extract the next sequential frame from the buffer and will pass this data
; to the caller.
;
; When called this unit assumes the buffer pointer is pointing at the first
; interval of the frame. That is, the value which should indicate the sync
; interval.
;
; This unit is used only for uplink telemetry and is interested only in the
; LSN and MSN fields of the frames. Each frames intervals will be summed
; until a time value is collected which exceeds the minimum LSN time. At
; this time the LSN will be calculated and summing will continue until the
; minimum MSN time is exceeded. After calculating the MSN value the data
; will be passed back to the caller in fr_data and the buffer pointer will
; be incremented to bypass the ending Pframe pulse interval.
;
; Any error in the frame will be returned in fr_stat as follows:
;
;           1xxxxxxx = Unused
;           x1xxxxxx = Unused
;           xx1xxxxx = No LSB pulse found
;           xxx1xxxx = No MSB pulse found
;           xxxx1xxx = Unused
;           xxxxx1xx = Unused
;           xxxxxx1x = Unused
;           xxxxxxx1 = Unused
;
; 1.2.1 GET_VAL UNIT
;
; Unit GET_VAL is called to extract the data value from table time_tab. It
; is called with r1,r2 = time interval - start of data field time and
; returns with the data value in the A register.
;
; 1.3 FLOW
;
; 1.3.1 PDL
;
;-      save the data pointer [push dph,dpl]
;       get interval buffer pointer [dph=bphi,dpl=bplo]
;       clear time accumulator [tac_hi,tac_lo2=0]
;       clear frame status [fr_stat = 0]
;       clear frame id [fr_id = 0]
;
; GETLSN:
;       get normalized interval [call GET_INT]
;       if not LSN [tac_hi,tac_lo < min_lsn]
;           get next interval [goto GETLSN]
;       endif

```
;      if missed LSN [tac_hi,tac_lo > max_lsn]
;          flag no LSN [set bit 5 fr_stat]
;          flag gain adjustment [call AGC_LOSS]
;          go check for MSN [goto GETMSN_CHK]
;      endif
;      compute LSN time [r1,r2 = tac_hi,tac_lo - min_lsn]
;      get table data [GET_VAL]
;      save data [fr_data = a]
;
; GETMSN:
;      get normalized interval [call GET_INT]
;
; GETMSN_CHK:
;      if not MSN [tac_hi,tac_lo < min_msn]
;          flag gain adjustment [call AGC_NOISE]
;          get next interval [goto GETMSN]
;      endif
;      if missed MSN [tac_hi,tac_lo > max_msn]
;          flag no MSN [set bit 4 fr_stat]
;          flag gain adjustment [call AGC_LOSS]
;          go exit [goto GF_EXIT]
;      endif
;      compute MSN time [r1,r2 = tac_hi,tac_lo - min_msn]
;      get table data [GET_VAL]
;      save data [fr_data = (a << 4) ORed with fr_data]
;
; GF_EXIT:
;      bump pointer past Pframe [dptr + 2]
;      save buffer pointer [bphi=dph, bplo=dpl]
;      restore dptr [pop dpl,dph]
;      return
;
;
;
; GET_INT:
;      get interval MSB from buffer [a=@dptr]
;      bump pointer [dptr+1]
;      save interval [r1=a]
;      get interval LSB [a=@dptr]
;      bump pointer [dptr+1]
;      save LSB [r2,a]
;      compute new time [tac_lo = tac_lo + r2]
;      compute new time [tac_hi = tac_lo + r1]
;      return to caller
;
;
; 1.4 CONSTRAINTS
;
; The higher level routine (TELEM) normalizes the intervals and corrects for
; error  caused by interrupt latency.
;
; 1.5 INPUT REQUIREMENTS:
;
; 1.5.1 PROCESSING:
;
; Corrected time intervals are placed into the interval buffer ($3500) by the
; calling routine.
;
```

```
; The interval buffer pointer (bphi, bplo) is initialized by the caller.
;
; 1.5.2 DATA ELEMENTS
;
;   bphi            interval buffer pointer MSB
;   bplo            interval buffer pointer LSB
;
; 1.6 OUTPUT REQUIREMENTS:
;
; 1.6.1 PROCESSING
;
; 1.6.2 DATA ELEMENTS
;
;   bphi            interval buffer pointer MSB
;   bplo            interval buffer pointer LSB
;   fr_stat         frame decode status
;   fr_id           frame id value
;   fr_data         frame data value
;
; 1.7 LOCAL DATA
;   r1.b2           pulse interval msb
;   r2.b2           pulse interval lsb
;   r4.b1           frame pulse counter
;
; 1.7.1 LOCAL EQUATES
;
;   lsn_min         min value for LSN field [717/1.5]
;   lsn_max         max value for LSN field [1204/1.5]
;   msn_min         min value for MSN field [1327/1.5]
;   msn_max         max value for MSN field [1814/1.5]
;
;
; 1.8 UNIT LEVEL TEST LIST
;
; <test #>   <test case description>     input values      output values
;
;     Check initialization.               dptr=1234h
;                                         bphi=56h
;                                         bplo=78h           dptr=5678h
;                                         tac_hi=12h         tac_hi=0
;                                         tac_lo=34h         tac_lo=0
;                                         fr_stat=ffh        fr_stat=0
;                                         fr_data=98h        fr_data=0
;                                                            end:GETLSN
;
;     Check GET_INT.                      start:GET_INT
;                                         dptr=3500h
;                                         $3500=12h
;                                         $3501=34h
;                                         r1=0               r1=12h
;                                         r2=ffh             r2=34h
;
;     Check GETLSN, good interval, first
;     try.                                start:GETLSN
;                                         dptr=3500h
;                                         fr_stat=0
;                                         tac_hi=0
;                                         tac_lo=0           fr_stat=0
```

```
;                                              $3500=02h        tac_hi=02
;                                              $3501=38h        tac_lo=38h
;                                                               r1=00
;                                                               r2=5Ah
;                                                               stop:GET_VAL
;
;   Check GETLSN, 2 short intervals           start:GETLSN
;   summing to valid LSN value.               dptr=3500h
;                                              $3500=01
;                                              $3501=70h        r1=00
;                                              $3502=0          r2=5Ah
;                                              $3503=c8h        stop:GET_VAL
;
;   Check GETLSN, missed LSN.                 start:GETLSN
;                                              dptr=3500h
;                                              $3500=03
;                                              $3501=7fh        fr_stat=20h
;                                              fr_stat=0        stop:AGC_LOSS
;
;   Check GETMSN, good interval, first
;   try.                                      start:GETMSN
;                                              dptr=3500h       r1=00
;                                              tac_hi=02        r2=99h
;                                              tac_lo=38h       fr_stat=0
;                                              fr_stat=0        tac_hi=04
;                                              fr_data=01       tac_lo=0dh
;                                              $3500=01h
;                                              $3501=d5h        stop:GET_VAL
;
;
;   Check GETMSN, 2 short intervals           start:GETMSN
;   summing to valid MSN value.               dptr=3500h
;                                              tac_hi=0
;                                              tac_lo=0
;                                              $3500=02
;                                              $3501=38h        r1=00
;                                              $3502=01         r2=99h
;                                              $3503=d5h        stop:AGC_NOISE
;
;   Check GETMSN, missed MSN.                 start:GETMSN
;
;       dptr=3500h
;                                              $3500=04
;                                              $3501=b6h        fr_stat=10h
;                                              fr_stat=0        stop:AGC_LOSS
;
;   Check exit code.                          start:GF_EXIT
;                                              stack=1122h
;                                              dptr=5678h
;                                              bphi=12h         bphi=56h
;                                              bplo=34h         bplo=7Ah
;                                                               dptr=1122h
;
;
; 1.9 UNIT LIST
;
;   AGC_NOISE        gain control noise adjustment
```

```
;    AGC_LOSS      gain control signal loss adjustment
;    GET_VAL       table look up
;
;
;
;---++/ $$$$$$$$$$$$$$$$$$$$$$$$$$$$$$$$$$$$$$$$$$$$$$$$$$$$$$$$$$$$$$$$$$

;---++/ $$$$$$$$$$$$$$$$$$$$$$$$$$$$$$$$$$$$$$$$$$$$$$$$$$$$$$$$$$$$$$$$$$
;
;
; 1 GET_VAL UNIT
;
; 1.1 CALLED BY:
;
;    GET_FRAME UNIT
;    DMARK UNIT
;
; 1.2 DESCRIPTION OF UNIT:
;
; This unit is used to extract the telemetry frame data value from table
; time_tab returning the data value in the A register.
;
; Note that an extra byte appears after every 60 bytes of table.  This is to
; compensate for the .5 usec error in table resolution incurred for each
; value group.
;
;
; 1.3 FLOW
;
; 1.3.1 PDL
;
;    save dptr [stack]
;    compute table index [dptr = time_tab + r1,r2]
;    get value from table [a = @dptr]
;    restore dptr [stack]
;    return to caller [a = data]
;
; 1.4 CONSTRAINTS
;
; This unit does NO range checking on the input value (r1, r2).  This
; must be done by the caller.
;
; 1.5 INPUT REQUIREMENTS:
;
; 1.5.1 PROCESSING:
;
;
; 1.5.2 DATA ELEMENTS
;
;    time_tab           interval translation table
;
;            TIME_TAB:
;                    DB   0,0,0,0,0,0,0,0,0,0
;                    DB   0,0,0,0,0,0,0,0,0,0
;                    DB   1,1,1,1,1,1,1,1,1,1
```

```
;                       DB      1,1,1,1,1,1,1,1,1,1
;                       DB      2,2,2,2,2,2,2,2,2,2
;                       DB      2,2,2,2,2,2,2,2,2,2
;                       DB      2
;                       DB      3,3,3,3,3,3,3,3,3,3
;                       DB      3,3,3,3,3,3,3,3,3,3
;                       DB      4,4,4,4,4,4,4,4,4,4
;                       DB      4,4,4,4,4,4,4,4,4,4
;                       DB      5,5,5,5,5,5,5,5,5,5
;                       DB      5,5,5,5,5,5,5,5,5,5
;                       DB      5
;                       DB      6,6,6,6,6,6,6,6,6,6
;                       DB      6,6,6,6,6,6,6,6,6,6
;                       DB      7,7,7,7,7,7,7,7,7,7
;                       DB      7,7,7,7,7,7,7,7,7,7
;                       DB      8,8,8,8,8,8,8,8,8,8
;                       DB      8,8,8,8,8,8,8,8,8,8
;                       DB      8
;                       DB      9,9,9,9,9,9,9,9,9,9
;                       DB      9,9,9,9,9,9,9,9,9,9
;                       DB      10,10,10,10,10,10,10,10,10,10
;                       DB      10,10,10,10,10,10,10,10,10,10
;                       DB      11,11,11,11,11,11,11,11,11,11
;                       DB      11,11,11,11,11,11,11,11,11,11
;                       DB      11
;                       DB      12,12,12,12,12,12,12,12,12,12
;                       DB      12,12,12,12,12,12,12,12,12,12
;                       DB      13,13,13,13,13,13,13,13,13,13
;                       DB      13,13,13,13,13,13,13,13,13,13
;                       DB      14,14,14,14,14,14,14,14,14,14
;                       DB      14,14,14,14,14,14,14,14,14,14
;                       DB      14
;                       DB      15,15,15,15,15,15,15,15,15,15
;                       DB      15,15,15,15,15,15,15,15,15,15
;
;
; 1.6 OUTPUT REQUIREMENTS:
;
; 1.6.1 PROCESSING
;
; 1.6.2 DATA ELEMENTS
;
;
; 1.7 LOCAL DATA
;       r1.bx           pulse interval msb
;       r2.bx           pulse interval lsb
;       time_tab        table of frame field values as follows (located
;                       in GET_FRAME)
;
; 1.7.1 LOCAL EQUATES
;
;
; 1.8 UNIT LEVEL TEST LIST
;
; <test #>    <test case description>     input values     output values
;
```

```
;           Check table lookup, 16 bit index.       dptr=1234h
;                                                   r1=01
;                                                   r2=2Ch          A=14
;                                                                   dptr=1234h
;
; 1.9 UNIT LIST
;
;       None.
;
;
;----++/ $$$$$$$$$$$$$$$$$$$$$$$$$$$$$$$$$$$$$$$$$$$$$$$$$$$$$$$$$$$$$$$$$$$$$

SKIP
;----**/$$$$$$$$$$$$$$$$$$$$$$$$$$$$$$$$$$$$$$$$$$$$$$$$$$$$$$$$$$$$$$$$$$$$$
;
;
; 1 AGC_NOISE UNIT
;
; 1.1 CALLED BY:
;
;       GET_FRAME
;
; 1.2 DESCRIPTION OF UNIT:
;
; This unit is called from GET_FRAME during the telemetry decoding process
; if an extra RF pulse is detected.
;
; The purpose of the unit is to flag a gain adjustment to the logic
; contained in the telemetry interrupt service routine (EXT0).
;
; Two flags are involved, "gain_adj" and "gain_up". The gain_adj flag
; indicates that the need for a gain adjustment has been determined. The
; gain_up flag tells EXT0 which way to move the gain.
;
; On entry to this unit the gain_adj flag is checked. If a noise adjustment
; has already been determined, the routine is exited. If a loss adjustment
; has been flagged, gain_adj is cleared and no adjustment is performed.
;
; 1.3 FLOW
;
; 1.3.1 PDL
;
;       if gain adjustment already flagged [gain_adj=1]
;           if adjustment is loss [gain_up=1]
;               clear adjustment required flag [gain_adj=0]
;           endif
;       else
;           set gain adjust required flag [gain_adj=1]
;           flag decrement gain [gain_up=0]
;       endif
;       return
;
; 1.4 CONSTRAINTS
;
; 1.5 INPUT REQUIREMENTS:
;
```

```
;   None.
;
; 1.6 OUTPUT REQUIREMENTS:
;
; 1.6.1 PROCESSING
;
;   None.
;
; 1.6.2 DATA ELEMENTS
;
;   gain_adj            gain adjustment required flag.
;   gain_up             increase gain flag.
;
; 1.7 LOCAL DATA
;
;   None.
;
; 1.8 UNIT LEVEL TEST LIST
;
; <test #>    <test case description>   input values    output values
;
;   1.    Check for flags set,           gain_adj=0      gain_adj=1
;                                        gain_up=1       gain_up=0
;
;   2.    Check for flags cancelling.    gain_adj=1      gain_adj=0
;                                        gain_up=1
;
;   3.    Check for no change if already set.
;                                        gain_adj=1      gain_adj=1
;                                        gain_up=0       gain_up=0
;
;
;
;
; 1.9 UNIT LIST
;
;   None.
;
;
;----++/ $$$$$$$$$$$$$$$$$$$$$$$$$$$$$$$$$$$$$$$$$$$$$$$$$$$$$$$$$$$$$$$$$$$$$$

SKIP
;----**/$$$$$$$$$$$$$$$$$$$$$$$$$$$$$$$$$$$$$$$$$$$$$$$$$$$$$$$$$$$$$$$$$$$$$$
;
;
; 1 AGC_LOSS UNIT
;
; 1.1 CALLED BY:
;
;       GET_FRAME
;
; 1.2 DESCRIPTION OF UNIT:
;
```

```
; This unit is called from GET_FRAME during the telemetry decoding process
; when missing RF pulse are detected.
;
; The purpose of the unit is to flag a gain adjustment to the logic
; contained in the telemetry interrupt service routine (EXT0).
;
; Two flags are involved, "gain_adj" and "gain_up". The gain_adj flag
; indicates that the need for a gain adjustment has been determined. The
; gain_up flag tells EXT0 which way to move the gain.
;
; On entry to this unit the gain_adj flag is checked. If a loss adjustment
; has already been determined, the routine is exited. If a noise adjustment
; has been flagged, gain_adj is cleared and no adjustment is performed.
;
;
;
;
; 1.3 FLOW
;
; 1.3.1 PDL
;
;       if gain adjustment already flagged [gain_adj=1]
;           if adjustment is noise [gain_up=0]
;               clear adjustment required flag [gain_adj=0]
;           endif
;       else
;           set gain adjust required flag [gain_adj=1]
;           flag increment gain [gain_up=1]
;       endif
;       return
;
;
; 1.4 CONSTRAINTS
;
; 1.5 INPUT REQUIREMENTS:
;
; 1.5.1 PROCESSING:
;
; 1.5.2 DATA ELEMENTS
;
;   .   None
;
; 1.6 OUTPUT REQUIREMENTS:
;
; 1.6.1 PROCESSING
;
;       None.
;
; 1.6.2 DATA ELEMENTS
;
;       gain_adj            gain adjustment required
flag.
;       gain_up             increase gain flag.
;
; 1.7 LOCAL DATA
;
;       None.
;
```

```
; 1.8 UNIT LEVEL TEST LIST
;
; <test #>    <test case description>     input values    output values
;
;    1.   Check for flags set,            gain_adj=0      gain_adj=1
;                                         gain_up=0       gain_up=1
;
;    2.   Check for flags cancelling.     gain_adj=1      gain_adj=0
;                                         gain_up=0
;
;    3.   Check for no change if already set.
;                                         gain_adj=1      gain_adj=1
;                                         gain_up=1       gain_up=1
;
;
; 1.9 UNIT LIST
;
;     None.
;
;
;---++/ $$$$$$$$$$$$$$$$$$$$$$$$$$$$$$$$$$$$$$$$$$$$$$$$$$$$$$$$$$$$$$$$$$$$$$$

;---**/$$$$$$$$$$$$$$$$$$$$$$$$$$$$$$$$$$$$$$$$$$$$$$$$$$$$$$$$$$$$$$$$$
;
;FILE NAME: idle_lib.S
;TASK NAME: LNKCHK
;FUNCTION:  GLOBAL SUPPORT FUNCTION
;
;1 LNKCHK
;
;1.1 CALLED BY:
;
;     Time out of pseudo timer 3.
;
;1.2 DESCRIPTION OF UNIT:
;
;     'LNKCHK' is a time scheduled task running once every 125 msec
;     to check the status of the telemetry channel. If the PPU is
;     busy, return, leave timer active. Otherwise, reset pseudo
;     timer 3 for 125 msec, send the 'check link status' command to
;     PPU and wait for completion. If the link status is unchanged
;     then exit, else the task updates the link status L.E.D. and
;     vectors to the 'Link Status Changed' handler if the link is
;     good.
;
;     'LNKCHK' also maintains the signal strength indicator displayed on line 2
;     of the LCD. The signal strength indicator consists of the string 'SIGNAL:'
;     and a signal strength value in the range 0-9. When the link is found to be
;     bad, the stability factor stored in the RAM variable STABILITY is
;     decreased. If the link is found to be good, the stability factor is
;     increased. Note that the amount the stability factor is decreased for a
;     bad link is significantly greater than the amount the stability factor is
;     increased for a good link. The displayed signal strength is derived from
;     the normalized gain value minus the stability factor. The value is clipped
;     to keep it within the 0-9 value range.
;
```

```
;       IF THE LINK GOES FROM BAD TO GOOD THEN THE DO_ANYWAY FLAG WILL
;       BE CHECKED, IF THIS FLAG IS NOT SET THEN THE ROUTINE WILL RETURN
;       IF THE FLAG IS SET THEN THE TIMER PT7 WILL BE CHECKED.  IF PT7 IS
;       ON THEN THE DO_ANYWAY FLAG WILL BE SET AND THE ROUTINE WILL
;       EXIT. IF THE TIMER IS NOT ACTIVE, THEN THE HANDLER WILL BE CALLED.
;
;1.2.1 SEND UNIT
;
;       This routine is called when a message is to be sent to the PPU.  A
;       message block is passed that contains the PPU command code followed by
;       any data that is to be sent.  The command byte is written to the command
;       register and the remaining data bytes are written one at a time to the
;       PPU data register.
;
;       Inputs:
;         DE - Address of block to send
;          C - Length of block to send
;         HL - Address of return status handler
;
;1.2.2 PPUGON UNIT
;
;       THIS ROUTINE IS GIVEN CONTROL WHEN THE PPU HAS FAILED TO RESPOND TO AN
;       OUTPUT REQUEST OR FAILED TO DELIVER DATA.  THE OPERATOR IS NOTIFIED AND
;       THE SYSTEM IS SHUT DOWN.  PC, FROM WHERE PPUGON IS CALLED, IS STORED
;       IN NON-VOLATILE RAM.
;
;1.2.3 HEXASC UNIT
;
;       Convert a 1 byte value to a 2 char ascii hex representation suffixed by
;       'H'.
;
;       Inputs:
;          A = HEX NUMBER    ( 1 BYTE)
;
;1.2.4 DISPLY UNIT
;
;       DISPLAYS CHARACTER MESSAGE ON 4 ROW X 40 COLUMN LCD DISPLAY.
;
;       Inputs:
;         [HL] = MESSAGE
;          C = ROW/COLUMN ADDRESS OF CHARACTER ON LCD
;          B = UNDERLINE FLAG:  80H - UNDERLINE THE MESSAGE
;                               00H - NO UNDERLINES
;
;1.3 FLOW
;
;1.3.1 PDL
;
; --CHECK OUT PPU--
;       if PPU is busy                              [[PPUSTS]<>0]
;       then set timer to return immediately        [[PT3]=0]
;            return
;       else reset timer to 125 ms.                 [[PT3]=0CH]
;            check link                             [DE=LNKMSG,C=1,SEND]
;            clear PPU status flag                  [[PPUSTS]=0]
;            set loop time out value                [B=0]
;            loop until PPU responds or time out
```

```
;       if no PPU response                          [[GSTAT] and DIFULL =0]
;         then decrement time out counter           [B=B-1]
;       endloop
;       if loop timed out                           [B=0]
;       then call PPU mortician (halt operation)    [PPUGON]
;       save link status                            [[PPDIN] to stack]

;--UPDATE SIGNAL STRENGTH INDICATION--
;       check gain status                           [DE=GAINMSG,C=1,SEND]
;       clear PPU status flag                       [[PPUSTS]=0]
;       set loop time out value                     [B=0]
;       loop until PPU responds or time out
;         if no PPU response                        [[GSTAT] and DIFULL =0]
;         then decrement time out counter           [B=B-1]
;       endloop
;       if loop timed out                           [B=0]
;       then call PPU mortician (halt operation)    [PPUGON]
;
;       normalize gain value:                       [A=[PPDIN]]
;         shift right twice                         [A=A/4]
;         compliment                                [A=CPL A]
;         mask off bits 3-7                         [A=A and 00000111B]
;         adjust to 2-9 value                       [A=A+2]
;         subtract out stability factor             [A=A-[STABILITY]]
;         if less than zero                         [C=1]
;         then set to zero                          [A=0]
;         else if greater than nine                 [A>9]
;           then set to nine                        [A=9]
;
;       convert gain to hex format                  [HEXASC,[HL]=string]
;       if ok to display signal strength            [[STR_FLG]=0FFH]
;       then save current test recording condition  [stack=[TEST_ON]]
;           turn off auto test recording            [TEST_ON.b4=0]
;           display gain value                      [BC=047H,DISPLY]
;           display 'SIGNAL:' string                [BC=40H,HL=NMSG,DISPLY]
;           restore auto test recording             [[TEST_ON=stack]

;--UPDATE STABILITY FACTOR--
;       restore link status                         [stack to AF]
;       if link status is not good                  [A<>0FFH]
;       then account for unstable link              [[STABILITY]=[STABILITY]+2C0H]
;       else account for more stable link           [[STABILITY]=[STABILITY]-0C0H]

;--UPDATE POSITION HEAD LED--CHECK FOR INTERROGATE CONDITIONS--
;       if link status has changed                  [POP AF, A<>[LINKST]]
;       then set LED control to current state
;           update RAM status
;           update 810 I/O controller
;           if previous link status is not good     [[LINKST]<>0FFH]
;           then return
;       else if link is bad                         [A<>0FFH]
;           then return
;           else if not OK to inter                 [[DO_ANYWAY]=0]
;               then return
;       if timer not on                             [[PT7]= 0 or 0FFH]
;       then vector to link change handler (exit)
;       else set inter flag for next pass           [[DO_ANYWAY]=1]
```

```
;        return
;
;1.4 CONSTRAINTS
;
;       none
;
;1.5 INPUT REQUIREMENTS:
;
;1.5.1 PROCESSING:
;
;       none
;
;1.5.2 DATA ELEMENTS
;
;       NAME                    DESCRIPTION
;       ----------              ---------------------------
;       PPUSTS                  PPU status flag
;       PT3                     Link check timer
;       GSTAT                   MPU status byte register
;       STABILITY               Link stability condition flag
;       STR_FLG                 Signal display flag, controls display of signal
;       LINKST                  Link status flag
;       DO_ANYWAY               Wait flag for Auto-Interrogate
;       PT7                     Interrogate retry timer
;       TEST_ON                 Auto test recording status flag
;
;1.6 OUTPUT REQUIREMENTS:
;
;1.6.1 PROCESSING
;
;       none
;
;1.6.2 DATA ELEMENTS
;
;       NAME                    DESCRIPTION
;       ----------              ---------------------------
;       PT3                     Link check timer
;       STABILITY               Link stability condition flag
;       DO_ANYWAY               Wait flag for Auto-Interrogate
;
;1.7 LOCAL DATA
;
;       MMSG                    'SIGNAL:' message
;       LNKMSG                  Check link status command
;       GAMMSG                  Check current gain value
;
;1.8 UNIT LEVEL TEST LIST
;
; TEST CASES:
;<test #>    <test case description>    input values    output values
;-------------------------------------  -------------   -------------
; A. If PPU is busy upon entry:         [PPUSTS]<>0
;    a) Verify PT3 reset to time out
;       immediately.                                    [PT3]=0
;    b) Verify unit exits.
;
; B. If PPU not busy upon entry:        [PPUSTS]=0
```

```
;   a) Verify link timer reset to
;      250 ns.                                              [PT3]=0CH
;
;   When checking link and gain status:    B decremented through all values
;   a) Verify no response from PPU         while waiting on PPU.
;      causes system halt.
;
; C. Verify gain normalized to values      PPDIN=0
;    within 2-9.
;
;   Verify "SIGNAL" displayed on LCD line 2.
;
;   Verify gain of 9 displayed on LCD line 2.
;
; D. Verify gain normalized to values      PPDIN=7
;    within 2-9.
;
;   Verify "SIGNAL" displayed on LCD line 2.
;
;   Verify gain of 0 displayed on LCD line 2.
;
; E. Like case D where PPDIN=7 but STR_FLAG is 0.
;
;   Verify "SIGNAL" and gain of 0 are NOT displayed on LCD line 2.
;
; F. With PPDIN <> OFFH, Cause Stability value to be incremented with No carry
;    If returned link status is bad:       link stat from stack <> OFFH
;    Verify stability factor adjusted.     [STABILITY]=[STABILITY]+2COH
;
; G. With PPDIN <> OFFH, Cause Stability value to be incremented with carry
;    If returned link status is bad:       link stat from stack <> OFFH
;    Verify stability factor adjusted.     [STABILITY]=[STABILITY]+2COH
;
;
; H. With PPDIN == OFFH, Cause Stability value to be decremented with No carry
;    If returned link status is good:      link stat from stack = OFFH
;    Verify stability factor adjusted.     [STABILITY]=[STABILITY]-0COH
;
;
; I. With PPDIN == OFFH, Cause Stability value to be decremented with carry
;    If returned link status is good:      link stat from stack = OFFH
;    Verify stability factor adjusted.     [STABILITY]=[STABILITY]-0COH
;
;
; J. with DO_ANYWAY=1, PPDIN=OFFH, LINKST=01FH, PT7 = 0, verify:
;
;    PORTCR bit 1 is cleared
;    DO_ANYWAY remains set to 1
;    [LINKSU] stub is vectored to
;    Unit returns with Z flag cleared
;
; K. with DO_ANYWAY=2, PPDIN=OFFH, LINKST=OFFH, PT7 = 0, verify:
;
;    PORTCR bit 1 is NOT cleared
;    DO_ANYWAY is NOT set to 1
;    [LINKSU] stub is vectored to
;    Unit returns with Z flag cleared
;
```

```
; L. with DO_ANYWAY=0, PPDIN=0FFH, LINKST=0FFH, PT7 = 0,  verify:
;
;     PORTCR bit 1 is NOT cleared
;     DO_ANYWAY is NOT set to 1
;     [LINKSV] stub is NOT vectored to
;     Unit returns with Z flag set
;
; M. with DO_ANYWAY=1, PPDIN=0FFH, LINKST=0FFH, PT7 = 0FFH,  verify:
;
;     PORTCR bit 1 is NOT cleared
;     DO_ANYWAY is set to 1
;     [LINKSV] stub is vectored to
;     Unit returns with Z flag cleared
;
; N. with DO_ANYWAY=2, PPDIN=0FFH, LINKST=02H, PT7 = 1,  verify:
;
;     PORTCR bit 1 is cleared
;     DO_ANYWAY is set to 1
;     [LINKSV] stub is NOT vectored to
;     Unit returns with Z flag cleared
;
;SLNKCHK:IDLE_LIB
;%INPUT
;;----------------------------------------------------------------
;; Type   Identifier       Input Data
;
; #include <chg_gstat.cfi>        ; re-map ppu registers, for direct control
; #include <cout.cfi>             ; re-map display primitives
;
; set_line2                 '*'
;
; nb     TEST_ENABLE   0                      ; Turn OFF default printer dumps!
;                      ; A B C D E F
; nb     STR_FLG       1,1,1,1,0,1            ; Signal Strength Flag 1=display
;
; nb     SEND          [0DDH,2AH,00H,0F6H, \  ; LD IX, [0F600H]
;                      0DDH,73H,00H, \        ; LD [IX+0],E
;                      0DDH,72H,01H, \        ; LD [IX+1],D
;                      0DDH,71H,02H, \        ; LD [IX+2],C
;                      0DDH,023H, \           ; INC IX
;                      0DDH,023H, \           ; INC IX
;                      0DDH,023H, \           ; INC IX
;                      0DDH,22H,00H,0F6H, \   ; LD [0F600H],IX
;                      0C9H],@                ; RET
;
; nw    0F600H         <0F602H>               ; where SEND writes
; nb:6  0F602H         0FFH                   ; init for 2 calls
;
; nb    0F630H         [00H, \                ; NOP
;                      0E5H, \                ; PUSH HL
;                      21H,08H,0F6H, \        ; LD HL, 0F608H
;                      034H, \                ; INC [HL]
;                      0E1H, \                ; POP HL
;                      0C9H],@                ; RET
;
; nw    LINKSV         <0F630H>               ; set Addr of LNKSV handler
; nb    0F608H         0                      ; # times LNKSV is vectored to
;
```

```
; nb    PPUGON:PPU_COM  [00H,00H],@              ;NOP so that we can stop on call
;
;
; r     A               55H                      ; init to known value
; nb    PT3             66H                      ;
; nb    TEST_ON         034H                     ;
;
; nb    PORTCR          0FFH                     ; Can't modify PORTC,
;                                                ; but PORTCR will be the same
;
;                       ; A B C D E F G H I
; nb    DO_ANYWAY       0,0,0,0,0,0,0,0,0,\      ; Case A-I  Must INTER
;                       1,2,0,1,2                ;
;
; nb    STABILITY       0,0,[0AH,00H], \         ; Cause no borrow case C
;                       [00H,0AH], \             ; Cause Borrow case D
;                       [00H,0AH], \             ; Cause Borrow case E
;                       [09H,00H], \             ; case F
;                       [00H,00H], \             ; case G
;                       [0BFH,00H], \            ; case H
;                       [05H,2CH]                ; case I
;
;                                                ; signal depends on PPDIN & STABILITY
; nb    PPDIN           0,0,0, \                 ; Case C, signal will be 9
;                       7, \                     ; Case D, signal will be 8
;                       7, \                     ; Case E, signal will be 8
;                       20, \                    ; Case F
;                       40, \                    ; Case G
;                       0FFH, \                  ; Case H
;                       02FH, \                  ; Case I
;                       0FFH                     ; Case J - end
;
;
;                       ; A B C D E F  G  H    I
; nb    LINKST          0,0,0,7,7,20,40,02FH,02FH,\  ; Case A-I LINKST same as PPDIN - exit via DO_ANYWAY=0
;                       01FH, \                  ; Case J - exit via bad link
;                       0FFH,0FFH,0FFH, \        ; Case K-M
;                       02H                      ; Case N
;
;                       ; A B C D E F G H I J K L M   N
; nb    PT7             0,0,0,0,0,0,0,0,0,0,0,0,0,0FFH,1
;
; nb    PPUSTS          1,0           ; 1 = PPU busy
;
; nb    GSTAT           @,0, DIFULL   ; Case B, set to no response
;
; e     @,PPUGON,@                    ; Case B, stop on call to PPUGON
;
;%OUTPUT
;;------------------------------------------------------------------------
;; Type  Identifier      Expected Output
;
; nb    TEST_ON 034H                  ; original value always saved
;
;                       ; A B C D E F G H I
```

```
; nb     DO_ANYWAY    0,0,0,0,0,0,0,0,0,\      ; Case A-I Must INTER
;                     1,2,0,1,1                ;
;
; nb     PT3          0,0CH
;
; nw     0F602H   @, <LNKMSG>                  ; DE - first call to SEND
; nb     0F604H   @, 1                         ; C - first call to SEND
;
; nw     0F605H   0FFFFH,0FFFFH, <GANMSG>      ; DE - second call to SEND
; nb     0F607H   0FFH, 0FFH,  1               ; C - second call to SEND
;
;              ; A B C D E F G H I J K L M N
; nb     0F608H   0,0,0,0,0,0,0,1,0,1,1,0,1,0  ; 1 if [LINKSV] Vectored to
;
; nb     PPUSTS       1,0,0
;
; nw     STABILITY    @,@,0CA02H, \            ; Case C ok as is
;                       0C009H, \              ; Case D set to 9
;                       0C009H, \              ; Case E set to 9
;                       0C902H, \              ; Case F
;                       0C002H, \              ; Case G
;                       0000H,  \              ; Case H
;                       0C509H, \              ; Case I
;                       @                      ; not testing cases J-end
;
;
; show_line2  @,@,\                                        ; Nothing for A-B
;             'SIGNAL:9***********************************',\   ; Case C
;             'SIGNAL:0***********************************',\   ; Case D
;             '********************************************',\  ; Case E
;             'SIGNAL:4***********************************',\   ; Case F
;             'SIGNAL:7***********************************',\   ; Case G
;             'SIGNAL:2***********************************',\   ; Case H
;             'SIGNAL:0***********************************',\   ; Case I
;             @                                            ; ignore case J-end
;
;              ; A B C D E F G H I J  K  L  M  N
; nb     PORTCR  @,@,@,@,@,@,@,@,@,0FEH,0FFH,0FFH,0FFH,0FEH
;
; r      F    x0xxxxxxB, \    ; Case A
;             @, \            ; Case B - doesn't matter
;             x0xxxxxxB, \    ; Case C - RET at DO_ANYWAY check
;             x0xxxxxxB, \    ; Case D - RET at DO_ANYWAY check
;             x0xxxxxxB, \    ; Case E - RET at DO_ANYWAY check
;             x0xxxxxxB, \    ; Case F - RET at DO_ANYWAY check
;             x0xxxxxxB, \    ; Case G - RET at DO_ANYWAY check
;             x0xxxxxxB, \    ; Case H - RET at DO_ANYWAY check
;             x0xxxxxxB, \    ; Case I - RET at DO_ANYWAY check
;             x0xxxxxxB, \    ; Case J - RET 'cause of BAD LINK
;             x0xxxxxxB, \    ; Case K
;             x1xxxxxxB, \    ; Case L - RET after DO_ANYWAY check
;             x0xxxxxxB, \    ; Case M
;             x0xxxxxxB       ; Case N
;
;
;1.9 UNIT LIST
;
```

```
;       NAME            STATUS                  DESCRIPTION
;       --------        ---------               -----------------------------------
;       SEND            NC                      sends command to PPU
;       PPUGON          NC                      embalms system
;       HEXASC          NC                      converts value to ASCII
;       DISPLY          NC
;
;
;---++/ $$$$$$$$$$$$$$$$$$$$$$$$$$$$$$$$$$$$$$$$$$$$$$$$$$$$$$$$$$$$$$$$$$
;
LNKCHK:
        LD      A,[PPUSTS]      ; IF PPU OPERATION IN PROGRESS
        OR      A               ;   THEN RETURN TO CALLER...
        LD      A,0CH           ;DO IT AGAIN IN 250 MS IF NO OPERATION
        JR      Z,LNK000        ;NO DELAY SO TIMER NEEDS 250
        LD      A,0             ;STILL NEED FLAG & NEED TO CHECK AGAIN SOON
LNK000: LD      [PT3],A
        RET     NZ              ;GO AROUND AGAIN LD      DE,LNKMSG
        LD      C,1
        CALL    SEND            ; SEND CHECK LINK MSG TO PPU
        XOR     A               ; CLEAR OUT OPERATION IN PROGRESS
        LD      [PPUSTS],A
        LD      B,0             ; FAIL SAFE TIME OUT VALUE = 256
LNK010:
        LD      A,[GSTAT]       ; CHECK FOR RESPONSE FROM PPU
        AND     DIFULL
        JP      NZ,LNK020
        DEC     B               ; NO RESPONSE YET, DECREMENT
        JP      NZ,LNK010       ;   FAIL SAFE AND REPEAT LOOP PUSH    BC              ; PPU
        PUSH    DE              ;   IS DEAD...
        PUSH    HL              ;      LONG LIVE THE PPU
        CALL    PPUGON          ;
LNK020:
        LD      A,[PPDIN]
        PUSH    AF              ;SAVE LINK STATUS LD      DE,GAMMSG
        LD      C,1
        CALL    SEND            ; SEND CHECK LINK MSG TO PPU
        XOR     A               ; CLEAR OUT OPERATION IN PROGRESS
        LD      [PPUSTS],A
        LD      B,0             ; FAIL SAFE TIME OUT VALUE = 256
LNK01X:
        LD      A,[GSTAT]       ; CHECK FOR RESPONSE FROM PPU
        AND     DIFULL
        JP      NZ,LNK02X
        DEC     B               ; NO RESPONSE YET, DECREMENT
        JP      NZ,LNK01X       ;   FAIL SAFE AND REPEAT LOOP PUSH    BC              ; PPU
        PUSH    DE              ;   IS DEAD...
        PUSH    HL              ;      LONG LIVE THE PPU
        CALL    PPUGON          ;
```

```
LNK02X:
        LD      A,[PPDIM]       ; CURRENT RF GAIN
        SRL     A               ; NORMALIZE VALUE
        SRL     A
        CPL                     ; INVERT IT
        AND     00000111B       ; MASK OTHER BITS (ONLY 0 - 7)
        ADD     A,2
        OR      A               ; CLEAR CARRY
        LD      DE,[STABILITY]  ; GET STABILITY INTO DE
        SBC     A,D             ; SUBTRACT OUT STABILITY FACTOR (USE MSB)
        JR      NC,NOB          ; NO BORROW
        LD      A,0             ; MIN SIGNAL LEVEL IS 0
NOB:
        CALL    HEXASC          ; CONVERT FOR DISPLAY
        LD      BC,047H         ; LINE 2 CHR 9D = 40H+9H
        PUSH    HL              ; load IY with pointer to string
        POP     IY
        LD      A,[IY+1]        ; get the digit we want to display
        LD      [HL],A          ; overwrite the first digit with the display digit
        XOR     A
        INC     HL              ; point to position following display digit
        LD      [HL],A          ; zero terminate display string
        DEC     HL              ; point to start of display string again LD      A,[STR_FLG]     ; CHECK FLAG FOR DISPLAY
        OR      A
        JR      Z,NO_DIS        ; NO DISPLAY LD      A,[TEST_ON]     ; GET AUTO TEST STATUS
        PUSH    AF              ; SAVE AUTO TEST STATUS
        RES     4,A             ; SET AUTO TEST TO OFF
        RES     0,A             ; SET AUTO TEST TO OFF
        LD      [TEST_ON],A
        CALL    DISPLY          ; DISPLAY SIGNAL STRENGTH VALUE
        LD      BC,40H
        LD      HL,NMSG         ; DISPLAY 'SIGNAL:' STRING
        CALL    DISPLY
        POP     AF              ; RETRIEVE AUTO TEST STATUS
        LD      [TEST_ON],A     ; RESTORE AUTO TEST STATUS
NO_DIS:
        POP     AF
        PUSH    AF              ; SAVE IT AGAIN
        LD      HL,[STABILITY]  ; GET STABILITY VALUE
        LD      DE,02C0H        ; INSTABILITY VALUE FOR BAD LINK
        CP      0FFH            ; CHECK FOR GOOD LINK
        JR      Z,LGOOD         ; LINK IS GOOD
        ADD     HL,DE           ; BUMP (IN)STABILITY UP
        LD      A,H
        CP      10
        JR      C,NOB2          ; NO CARRY (MAX 7)
        LD      A,9
        JR      NOB2
LGOOD:
        LD      DE,0C0H         ; STABILITY VALUE FOR GOOD LINK
        OR      A
        SBC     HL,DE           ; DEC (IN)STABILITY
        LD      A,H
        JR      NC,NOB2
        LD      A,0
```

*CALCULATE SIGNAL*

*DISPLAY SIGNAL:*

*STABILITY UPDATE*

```
            LD      L,0             ;MIN STABILITY 0
MOB2:       LD      [STABILITY+1],A ;STORE MSB
            LD      A,L
            LD      [STABILITY],A
            POP     AF              ;GET LINK STATUS BACK
            LD      HL,LINKST       ; IF STATUS HAS NOT CHANGED,
            CP      [HL]            ;
            JR      NZ,LNK021       ;
            CP      0FFH            ;IF LINK BAD THEN RETURN TO CALLER
            RET     NZ              ;LINK IS BAD NOW.
            LD      A,[DO_ANYWAY]   ;CHECK TO SEE IF WE INTER ANYWAY
            OR      A
            JR      NZ,LNK022       ;MUST INTER
            RET                     ;RETURN

LNK021:     LD      [HL],A          ;          AND PASS CONTROL TO HANDLER.

CPL                     ; COMPLEMENT THE BITS.
            AND     LEDCTL          ; ISOLATE LED CONTROL BIT
            LD      C,A             ; AND SAVE IT
            LD      A,[PORTCR]      ; GET CURRENT STATUS OF PORT C
            AND     0FFH-LEDCTL     ; FORCE LED CONTROL BIT OFF.
            OR      C               ; SET LED CONTROL TO CURRENT STATE
            LD      [PORTCR],A      ; UPDATE RAM STATUS.
            LD      [PORTC],A       ;    AND 810 I/O CONTROLLER

LD      A,[LINKST]      ;ONLY VECTOR IF LINK IS GOOD
            CP      0FFH            ;
            RET     NZ              ;LINK BAD
;
;
LNK022:     LD      A,[PT7]         ;IF TIMER NOT ON THEN
            INC     A               ;(NOT ON MEANS =0 OR FFH)
            AND     0FEH            ;TEST BIT 0 CHECKS BOTH CASES
            JR      Z,LNK023        ;IS OK TO INTER - TIMER OFF
            LD      A,1             ;SET DO_ANYWAY FLAG FOR NEXT PASS
            LD      [DO_ANYWAY],A
            RET                     ;MUST WAIT
;
LNK023:
            LD      HL,[LINKSV]     ; VECTOR TO LINK CHANGE HANDLER.
            JP      [HL]            ; ...EXIT...

LNKMSG:     DEFB    07              ; CHECK LINK STATUS COMMAND
GANMSG:     DEFB    13H             ; CHECK CURRENT GAIN VALUE

SKIP
;
;---**/$$$$$$$$$$$$$$$$$$$$$$$$$$$$$$$$$$$$$$$$$$$$$$$$$$$$$$$$$$$$$
```

What is claimed is:

1. In a software-controlled, external programmer for programming by downlink telemetry and receiving by uplink telemetry, data to and from an implanted medical device, the improved method for automatically optimizing gain level to minimize interference in the presence of noise in the uplink telemetry mode, comprising the steps of:

providing in said programmer an adjustable gain amplifier dependent upon a gain control input signal gain value for amplifying uplink telemetry radio frequency signals;

detecting uplink telemetry signals amplified by said amplifier which match detect criteria;

setting the gain control input signal applied to said amplifier to a minimum gain value;

starting a first time interval upon setting the gain value;

incrementing said gain value by a predetermined gain factor if no telemetry signal is detected within said first time interval;

comparing said incremented gain value to a maximum gain value and resetting said gain value to said minimum gain value each time said incremented gain value reaches said maximum gain value;

restarting said first time interval when an amplified signal is detected;

measuring the time interval between successive detected uplink telemetry signals and comparing said time interval to first and second formatted data intervals;

incrementing said gain value by said predetermined factor when the measured interval between successive telemetry signals exceeds both formatted data intervals; and decrementing said gain value by a decrement gain value factor whenever said interval between successive telemetry signals is less than but not equal to said first and second formatted intervals, whereby said gain value linearly increases and decreases as a function of the interval between telemetry signals.

2. The method of claim 1 further comprising the steps of:

complementing and scaling said gain value to provide a numeric value indicative of relative signal strength; and displaying said numeric value to the user of the programmer in order to simplify positioning of said programmer in relation to said medical device to optimize data transmission.

3. In a software-controlled, external programmer for programming by downlink telemetry and receiving by uplink telemetry, data to and from an implanted medical device, the improvement for automatically optimizing gain level to minimize interference in the presence of noise in the uplink telemetry receive mode, comprising:

an adjustable gain amplifier in said programmer dependent upon a gain control input signal gain value for amplifying uplink telemetry radio frequency signals;

means for detecting uplink telemetry signals amplified by said amplifier which match detect criteria;

means for setting the gain control input signal applied to said amplifier to a minimum gain value;

means for starting a first time interval upon setting the gain value;

means for incrementing said gain value by a predetermined gain factor if no telemetry signal is detected within said first time interval;

means for comparing said incremented gain value to a maximum gain value and resetting said gain value to said minimum gain value each time said incremented gain value reaches said maximum gain value;

means for restarting said first time interval when an amplified signal is detected;

means for measuring the time interval between successive detected uplink telemetry signals- and comparing said time interval to first and second formatted data intervals;

means for incrementing said gain value by said predetermined factor when the measured interval between successive telemetry signals exceeds both formatted data intervals; and means for decrementing said gain value by a decrement gain value factor whenever said interval between successive telemetry signals is less than but not equal to said first and second formatted intervals, whereby said gain value linearly increases and decreases as a function of the interval between telemetry signals.

4. The apparatus of claim 3 further comprising:

means for complementing and scaling said gain provide a numeric value indicative of relative signal strength; and means for displaying said numeric value to the user of the programmer in order to simplify positioning of said programmer in relation to said medical device to optimize data transmission.

5. In a software-controlled, external programmer for transcutaneously programming by downlink telemetry and receiving by uplink telemetry data to and from an implanted medical device, the improved apparatus for automatically minimizing interference in the presence of noise comprising:

adjustable gain amplifier means dependent upon a gain control input signal gain value for amplifying uplink telemetry data signals and providing an output signal;

threshold detector means for comparing said output signal to preselected detect criteria and providing a telemetry detect signal each time said output signal meets said detect criteria;

means for measuring the time intervals between successive detect signals and providing detect intervals;

gain control signal establishing means for providing said gain control input signal gain value in a range between a minimum and maximum value as a function of the detect intervals further comprising:

means for initially setting said gain value to a predetermined low gain initial value within said range;

means for increasing said gain value in the absence of detect signals within a first predetermined time interval;

means for comparing said incremented gain value to a maximum gain value and resetting said gain value to said minimum gain value each time said incremented gain value reaches said maximum gain value.

6. The apparatus of claim 5 further comprising:

means for establishing at least first and second data bit reference intervals;

means for comparing each detect interval to said first and second data bit reference intervals and providing a first signal each time said detect interval exceeds the longer of said data bit intervals, a second signal each time said detect interval is less than but not equal to either one or the other of said data bit reference intervals, and a third signal each time said detect interval matches a data bit interval; and means for increasing said gain value in response to said first signal, decreasing said gain value in response to a second signal, and maintaining said gain value in response to a third signal.

7. The apparatus of claim 5 further comprising:

means for establishing a reference data frame interval and a reference sync interval; and means for comparing each detect interval to said frame interval and increasing said gain value when said detect interval exceeds said frame interval and decreasing said gain value when said detect interval is less than said sync interval.

8. The apparatus of claim 7 wherein said comparing means provides a sync detect signal each time a detect interval matches a sync interval, and further comprising:
   means responsive to a sync detect signal for counting subsequent detect intervals within said data frame interval and providing a detect interval count;
   means for comparing said count to a frame reference count; and
   means for increasing said gain value when said count is less than said reference count and decreasing said gain value when said count is greater than said reference count.

9. In a software controlled, external programmer for transcutaneously programming by downlink telemetry and receiving by uplink telemetry data to and from an implanted medical device, the improvement for automatically minimizing interference in the presence of noise and providing a real time indication of the uplink telemetry signal strength to the user of the programmer comprising:
   adjustable gain amplifier means dependent upon a gain control input signal gain value for amplifying uplink telemetry
   thereshold detector means for comparing said output signal data signals and providing an output signal; to preselected detect criteria and providing a telemetry detect signal each time said output signal meets said detect criteria;
   means for measuring the time intervals between successive detect signals and providing detect intervals;
   gain control signal establishing means for providing said gain control input signal gain value in a range between a minimum and maximum value as a function of the detect intervals;
   means for complementing and scaling said gain value to provide a signal strength indication numeric value between a minimum and maximum value; and
   means for displaying said signal strength value to the user of the programmer in order to simplify positioning of said programmer in relation to said medical device to optimize data transmission.

10. The apparatus of claim 9 further comprising means for stabilizing said signal strength value.

11. In a software controlled, external programmer for transcutaneously programming by downlink telemetry and receiving by uplink telemetry data to and from an implanted medical device, the improved method for automatically minimizing interference in the presence of noise comprising the steps of:
   amplifying uplink telemetry data signals as a function of a gain control input signal gain value and providing an output signal;
   comparing said output signal to preselected detect criteria and providing a telemetry detect signal each time said output signal meets said detect criteria;
   measuring the time intervals between successive detect signals and providing detect intervals;
   providing said gain control input signal gain value in a range between a minimum and maximum value as a function of the detect intervals further comprising:
   initially setting said gain value to a predetermined low gain initial value within said range;
   increasing said gain value in the absence of detect signals within a first predetermined time interval; and
   decreasing said gain value to said initial value when the increased gain value equals or exceeds the maximum gain value.

12. The method of claim 11 further comprising:
   establishing at least first and second data bit reference intervals;
   comparing each detect interval to said first and second data bit reference intervals and providing a first signal each time said detect interval exceeds the longer of said data bit intervals, a second signal each time said detect interval is less than but not equal to either one or the other of said data bit reference intervals, and a third signal each time said detect interval matches a data bit interval; and
   increasing said gain value in response to said first signal, decreasing said gain value in response to a second signal, and maintaining said gain value in response to a third signal.

13. The method of claim 11 further comprising:
   establishing a reference data frame interval and a reference sync interval; and
   comparing each detect interval to said frame interval and increasing said gain value when said detect interval exceeds said frame interval and decreasing said gain value when a sync interval is expected and said detect interval is less than said sync interval.

14. The method of claim 13 wherein said comparing step provides a sync detect signal each time a detect interval matches a sync interval, and further comprising the steps of:
   counting said detect intervals within said data frame interval and providing a detect interval count;
   comparing said count to a frame reference count; and
   increasing said gain value when said count is less than said reference count and decreasing said gain value when said count is greater than said reference count.

15. In a software-controlled, external programmer for transcutaneously programming by downlink telemetry and receiving by uplink telemetry data to and from an implanted medical device, the improved method for automatically minimizing interference in the presence of noise and providing a real-time indication of the uplink telemetry signal strength to the user of the programmer steps of:
   amplifying uplink telemetry data signals as a function of a gain control input signal gain value and providing an output signal;
   comparing said output signal to preselected detect criteria and providing a telemetry detect signal each time said output signal meets said detect criteria;
   measuring the time intervals between successive detect signals and providing detect intervals;
   providing said gain control input signal gain value in a range between a minimum and maximum value as a function of the detect intervals;
   complementing and scaling said gain value to provide a signal strength indication numeric value between a minimum and maximum value; and
   displaying said signal strength value to the user of the programmer in order to simplify positioning of said programmer in relation to said medical device to optimize data transmission.

16. The method of claim 15 further comprising the step of stabilizing said signal strength value.

* * * * *

UNITED STATES PATENT AND TRADEMARK OFFICE
CERTIFICATE OF CORRECTION

PATENT NO. : 5,107,833
DATED : April 28, 1992
INVENTOR(S) : Michael S. Barsness

It is certified that error appears in the above-indentified patent and that said Letters Patent is hereby corrected as shown below:

Column 7, Line 26, after "steps.", please add --In conjunction with the main--.

Column 8, Line 61, delete "ne", and insert in its place --new--.

Column 21, Line 21, after "detected," insert --flag--

Column 21, line 22, after "counter", insert --and--.

Column 96, Line 9, after "gain", add --value to--.

Column 97, line 27, after "telemetry", add --data signals and providing an output signal;--.

Column 97, Line 28, after first occurrence of "signal", delete --data signals and providing an output signal;--.

UNITED STATES PATENT AND TRADEMARK OFFICE
CERTIFICATE OF CORRECTION

PATENT NO. : 5,107,833

DATED : April 28, 1992

INVENTOR(S) : Michael S. Barsness

It is certified that error appears in the above-indentified patent and that said Letters Patent is hereby corrected as shown below:

Column 98, Line 48-49, after "programmer", add --comprising the--.

Signed and Sealed this

Twenty-seventh Day of September, 1994

Attest:

BRUCE LEHMAN

Attesting Officer

Commissioner of Patents and Trademarks